United States Patent
Rollins et al.

(10) Patent No.: US 7,592,291 B2
(45) Date of Patent: Sep. 22, 2009

(54) METHOD OF FABRICATING A CATALYTIC STRUCTURE

(75) Inventors: Harry W. Rollins, Idaho Falls, ID (US); Lucia M. Petkovic, Idaho Falls, ID (US); Daniel M. Ginosar, Idaho Falls, ID (US)

(73) Assignee: Batelle Energy Alliance, LLC, Idaho Falls, ID (US)

( * ) Notice: Subject to any disclaimer, the term of this patent is extended or adjusted under 35 U.S.C. 154(b) by 92 days.

(21) Appl. No.: 11/688,930

(22) Filed: Mar. 21, 2007

(65) Prior Publication Data

US 2008/0045400 A1 Feb. 21, 2008

Related U.S. Application Data

(63) Continuation-in-part of application No. 11/464,566, filed on Aug. 15, 2006.

(51) Int. Cl.
*B01J 23/06* (2006.01)
*B01J 23/72* (2006.01)
*B01J 35/08* (2006.01)

(52) U.S. Cl. .............. 502/343; 502/8; 502/345
(58) Field of Classification Search .......... 502/8, 502/343, 345
See application file for complete search history.

(56) References Cited

U.S. PATENT DOCUMENTS

| | | | | |
|---|---|---|---|---|
| 3,615,217 A | * | 10/1971 | O'Brien et al. | 423/656 |
| 3,702,886 A | | 11/1972 | Argauer et al. | |
| 3,907,715 A | * | 9/1975 | Arai et al. | 502/320 |
| 4,863,894 A | * | 9/1989 | Chinchen et al. | 502/342 |
| 5,043,307 A | | 8/1991 | Bowes et al. | |
| 5,344,849 A | | 9/1994 | Ayasse | |
| 5,348,643 A | | 9/1994 | Absil et al. | |
| 5,348,924 A | | 9/1994 | Potter et al. | |
| 5,366,948 A | | 11/1994 | Absil et al. | |
| 5,378,440 A | | 1/1995 | Herbst et al. | |
| 5,456,821 A | | 10/1995 | Absil et al. | |
| 5,466,646 A | | 11/1995 | Moser | |
| 5,506,273 A | | 4/1996 | Haruta et al. | |
| 5,536,894 A | | 7/1996 | Degnan et al. | |

(Continued)

OTHER PUBLICATIONS

Baerlocher et al., "Atlas of Zeolite Framework Types," 5th Rev. ed., Elsevier, pp. 1-19 (with attached Framework Type Data Sheets) (2001).

(Continued)

Primary Examiner—Timothy C Vanoy
Assistant Examiner—Daniel Berns
(74) Attorney, Agent, or Firm—TraskBritt

(57) ABSTRACT

A precursor to a catalytic structure comprising zinc oxide and copper oxide. The zinc oxide has a sheet-like morphology or a spherical morphology and the copper oxide comprises particles of copper oxide. The copper oxide is reduced to copper, producing the catalytic structure. The catalytic structure is fabricated by a hydrothermal process. A reaction mixture comprising a zinc salt, a copper salt, a hydroxyl ion source, and a structure-directing agent is formed. The reaction mixture is heated under confined volume conditions to produce the precursor. The copper oxide in the precursor is reduced to copper. A method of hydrogenating a carbon oxide using the catalytic structure is also disclosed, as is a system that includes the catalytic structure.

22 Claims, 11 Drawing Sheets

U.S. PATENT DOCUMENTS

| | | | |
|---|---|---|---|
| 5,689,024 | A | 11/1997 | Schmitt |
| 5,695,735 | A | 12/1997 | Benazzi et al. |
| 5,786,294 | A | 7/1998 | Sachtler et al. |
| 5,919,430 | A | 7/1999 | Hasenzahl et al. |
| 5,955,049 | A | 9/1999 | Ogata et al. |
| 6,121,187 | A | 9/2000 | Maier |
| 6,297,180 | B1 | 10/2001 | Maier |
| 6,403,743 | B1 | 6/2002 | Clark et al. |
| 6,497,812 | B1 | 12/2002 | Schinski |
| 6,620,402 | B2 | 9/2003 | Jacobsen et al. |
| 6,620,983 | B1 | 9/2003 | Cao et al. |
| 6,627,572 | B1 | 9/2003 | Cai et al. |
| 6,638,892 | B1 | 10/2003 | Wu et al. |
| 6,680,278 | B2 | 1/2004 | Cao et al. |
| 6,686,511 | B2 | 2/2004 | Miller et al. |
| 6,706,936 | B2 | 3/2004 | O'Rear et al. |
| 6,812,373 | B2 | 11/2004 | Wang |
| 6,841,711 | B2 | 1/2005 | Krug et al. |
| 6,914,030 | B2 | 7/2005 | Cao et al. |
| 6,936,566 | B2 | 8/2005 | Mees et al. |
| 6,982,287 | B2 | 1/2006 | Wang et al. |
| 6,989,470 | B2 | 1/2006 | Wang |
| 7,005,118 | B2 | 2/2006 | Terres Rojas et al. |
| 7,022,888 | B2 | 4/2006 | Choudhary et al. |
| 7,048,781 | B1 | 5/2006 | Lovell |
| 7,064,097 | B1 | 6/2006 | Cai et al. |
| 2004/0064008 | A1 | 4/2004 | Maurer et al. |
| 2004/0234823 | A1 | 11/2004 | Burgener, II et al. |

OTHER PUBLICATIONS

Bessell, Sandra, "Support effects in cobalt-based Fisher-Tropsch catalysis," Applied Catalysis A: General 96: 253-268 (1993).

Cundy et al., "The Hydrothermal Synthesis of Zeolites: History and Development from the Earliest Days to the Present Time," Chem. Rev. 103: 663-701 (2003).

"Fischer-Tropsch process," Wikipedia, <<hhttp://en.wikipedia.org/wiki/Fischer-Tropsch>> 3 pages (2006).

Fornasari et al., "Cobalt-Modified Cu-Zn-Cr Catalysts in the Synthesis of Methanol," Journal of Catalysis, 135: 386-399 (1992).

Fukuoka et al., "Ship-in-bottle synthesis and catalytic performances of platinum carbonyl clusters, nanowires, and nanoparticles in micro- and mesoporous materials," Catalysis Today 66: 23-31 (2001).

Fujitani et al., "Methanol Synthesis for CO and $CO_2$ Hydrogenations over Supported Palladium Catalysts," Bull. Chem. Soc. Jpn., 75: 1393-1398 (2002).

Fujiwara et al., "Change of catalytic properties of Fe-ZnO/zeolite composite catalyst in the hydrogenation of carbon dioxide," Applied Catalysis A: General 154: 87-101 (1997).

Fujiwara, et al., "Hydrogenation of carbon dioxide over copper-pyrochlore/zeolite composite catalysts," Catalysis Today 29: 343-348 (1996).

Hadjigeorghiou et al., "Fischer-Tropsch Activity in $NiO-ThO_2$ Catalysts," Applied Catalysis, 21: 47-59 (1986).

Hartmann et al., "Transition-Metal Ions in Aluminophosphate and Silicoaluminophosphate Molecular Sieves: Location, Interaction with Adsorbates and Catalytic Properties," Chemical Reviews, vol. 99, No. 3 (1999).

Iwasa et al., "Methanol synthesis from $CO_2$ under atmospheric pressure over supported Pd catalysts," Catalysis Letters, vol. 96, Nos. 1-2: 75-78 (2004).

Klier, K., "Structure and Function of Real Catalysts," Applications of Surface Science, 19: 267-297 (1984).

Kniep et al., "Rational Design of Nanostructured Copper-Zinc Oxide Catalysts for the Steam Reforming of Methanol," Angew. Chem. Int. Ed. 2004, 43, 112-115.

Komatsu et al., "Fischer-Tropsch synthesis on RuTi intermetallic compound catalyst," Applied Catalysis A: General 279: 173-180 (2005).

Li et al., "Direct synthesis of middle *iso*-paraffins from synthesis gas," Catalysis Today 84: 59-65 (2003).

Li et al., "Direct synthesis of middle iso-paraffins from synthesis gas on hybrid catalysts," Catalysis Today 89: 439-446 (2004).

Liaw et al., "Liquid-phase synthesis of methanol from $CO_2/H_2$ over ultrafine CuB catalysts," Applied Catalysis A: General 206: 245-256 (2001).

Liu et al., "Surface active structure of ultra-fine $Cu/ZrO_2$ catalysts used for the $CO_2 + H_2$ to methanol reaction," Applied Catalysis A: General 218: 113-119 (2001).

Liu et al., "Recent Advances in Catalysts for Methanol Synthesis via Hydrogenation of CO and $CO_2$," Ind. Eng. Chem. Res. 42: 6518-6530 (2003).

Lok et al., "Silicoaluminophosphate Molecular Sieves: Another New Class of Microporous Crystalline Inorganic Solids," J. Am. Chem. Soc., 106: 6092-6093 (1984).

Maitlis et al., "Towards a chemical understanding of the Fischer-Tropsch reaction: alkene formation," Applied Catalysis A: General 186: 363-374 (1999).

Meier, W.M., "Zeolites and zeolite-like materials," Pure & Appl. Chem., vol. 58, No. 10, pp. 1323-1328 (1986).

Melián-Cabrera et al., "Pd-Modified Cu-Zn Catalysts for Methanol Synthesis from $CO_2/H_2$ Mixtures: Catalytic Structures and Performance," Journal of Catalysis 210: 285-294 (2002).

"Methanol and Methanol Derivative," pp. 29-47 (before Aug. 2, 2006).

Nakatsuji et al., "Mechanism of Methanol Synthesis on Cu(100) and Zn/Cu(100) Surfaces: Comparative Dipped Adcluster Model Study," International Journal of Quantum chemistry, vol. 77, 341-349 (2000).

Nam et al., "Catalytic conversion of carbon dioxide into hydrocarbons over iron supported on alkali ion-exchanged Y-zeolite catalysts," Applied Catalysis A: General 179: 155-163 (1999).

Park et al., "Catalytic Reduction of Carbon Dioxide," Energy Convers. Mgmt., vol. 36, No. 6-9, pp. 573-576 (1995).

Patterson et al., "Carbon monoxide hydrogenation over molybdenum and tungsten carbides," Applied Catalysis A: General 251: 449-455 (2003).

Ponec, V., "Active Centres for Synthesis Gas Reactions," Catalysis Today, 12 (1992) 227-254.

"The Production of Methanol and Gasoline," VII-Energy-D-Methanol, pp. 1-19 (before Aug. 2, 2006).

Riedel et al., "Comparative study of Fischer-Tropsch synthesis with $H_2/CO$ and $H_2/CO_2$ syngas using Fe- and Co-based catalysts," Applied Catalysis A: General 186: 201-213 (1999).

Saito et al., "Development of Cu/ZnO-Based High Performance Catalysts for Methanol Synthesis by $CO_2$ Hydrogenation," Energy Convers. Mgmt. vol. 36, No. 6-9, pp. 577-580 (1995).

Schmidt et al., "Carbon Nanotube Templated Growth of Mesoporous Zeolite Single Crystals," Chem. Mater. 13: 4416-4418 (2001).

Shannon et al., "Characterization of Catalytic Surfaces by Isotopic-Transient Kinetics during Steady-State Reaction," Chem. Rev. 95: 677-695 (1995).

Song et al., "Direct synthesis of isoalkanes through Fischer-Tropsch reaction on hybrid catalysts," Applied Catalysis A: General 110: 121-136 (1994).

Stöcker, Michael, "Methanol-to-hydrocarbons: catalytic materials and their behavior," Microporous and Mesoporous Materials, 29: 3-48 (1999).

Toyir et al., "Catalytic performance for $CO_2$ conversion to methanol of gallium-promoted copper-based catalysts: influence of metallic precursors," Applied Catalysis B: Environmental 34: 255-266 (2001).

Tsubaki et al., "Three-component hybrid catalyst for direct synthesis of isoparaffin via modified Fischer-Tropsch synthesis," Catalysis Communications 4: 108-111 (2003).

Xu et al., "The promotions of MnO and $K_2O$ to Fe/silicalite-2 catalyst for the production of light alkenes from $CO_2$ hydrogenation," Applied Catalysis A: General 173: 19-25 (1998).

Xu et al., "Hydrogenation of carbon dioxide over Fe-Cu-Na/zeolite composite catalysts: Na migration via solid-solid reaction and its effects on the catalytic activity," Journal of Molecular Catalysis A: Chemical 136: 161-168 (1998).

Xu et al., "Improved activity of Fe-Cu catalysts by physical mixing with zeolites for the hydrogenation of carbon dioxide," Journal of Molecular Catalysis A: Chemical 120: L23-L26 (1997).

Yao et al., "Ultrasound as a tool to synthesize nano-sized silica-alumina catalysts with controlled mesoporous distribution by a novel sol-gel process," Catalysis Letters, vol. 78, Nos. 1-4: 37-41 (2002).

Yin et al., "Mesoporous HMS molecular sieves supported cobalt catalysts for Fischer-Tropsch synthesis," Microporous and Mesoporous Materials 47: 15-24 (2001).

Zhang et al., "CO and $CO_2$ hydrogenation study on supported cobalt Fischer-Tropsch synthesis catalysts," Catalysis Today 71: 411-418 (2002).

Agny et al., "Synthesis of Methanol from Carbon Monoxide and Hydrogen Over a Copper-ZincOxide-Alumina Catalyst," Ind. Eng. Chem. Prod.Res.Dev. (1985) 24:50-55.

Govind et al., "Zeolite-Catalyzed Hydrocarbon Formation From Methanol: Denisty Functional Simulations," Int. J. Mol. Sci. (2002) 3:423-434.

Kresge et al., "Ordered Mesoporous Molecular Sieves Synthesized by a Liquid-Crystal Template Mechanism," Nature (1992) 359:710-712.

Tang et al., "Mono-sized single-Walled Carbon Nanotubes Formed in Channels of ALPO4-5 Single Crystal," Applied Physics Letters, Oct. 19, 1998, 73:2287-2289.

* cited by examiner

METHOD OF FABRICATING A CATALYTIC STRUCTURE

CROSS-REFERENCE TO RELATED APPLICATION

This application is a continuation-in-part of U.S. patent application Ser. No. 11/464,566, entitled "Structures Including Catalytic Materials Disposed Within Porous Zeolite Materials, Systems And Methods For Using The Same, And Methods Of Fabricating Catalytic Structures," filed Aug. 15, 2006, pending, the disclosure of which is incorporated by reference herein in its entirety and which is assigned to the assignee hereof.

STATEMENT REGARDING FEDERALLY SPONSORED RESEARCH OR DEVELOPMENT

The United States Government has certain rights in this invention pursuant to Contract No. DE-AC07-05ID14517 between the United States Department of Energy and Battelle Energy Alliance, LLC.

FIELD OF THE INVENTION

The present invention relates to catalytic materials, systems, and methods. More particularly, the present invention relates to precursor catalytic structures including copper oxide and zinc oxide, catalytic structures including copper and zinc oxide, and to a system and a method for producing alcohols from hydrogen and at least one of carbon monoxide and carbon dioxide using such catalytic structures. The present invention also relates to methods of fabricating such catalytic structures.

BACKGROUND OF THE INVENTION

Carbon dioxide gas ($CO_2$) may be converted into liquid fuels such as, for example, hydrocarbon molecules of between about 5 and about 12 carbon atoms per molecule (e.g., gasoline) through multi-step reactions. For example, carbon dioxide ($CO_2$) gas and hydrogen ($H_2$) may be converted to carbon monoxide (CO) gas and water ($H_2O$) through the Reverse Water-Gas Shift Reaction, which is shown by Reaction [1] below.

$$CO_2 + H_2 \rightarrow CO + H_2O \qquad [1]$$

Synthesis gas, which is a mixture of carbon monoxide gas (CO) and hydrogen gas ($H_2$) then may be produced from the reaction products of the Reverse Water-Gas Shift Reaction by adding additional hydrogen gas ($H_2$) to the reaction products. This synthesis gas may be further reacted through either Fischer-Tropsch (FT) processes, or through methanol synthesis (MS) plus methanol-to-gasoline (MTG) processes, to provide liquid fuels.

Briefly, Fischer-Tropsch processes include various catalyzed chemical reactions in which synthesis gas is converted into liquid hydrocarbons in a reactor in the presence of a catalyst and at temperatures between about 200° C. and about 350° C. Catalysts used in Fischer-Tropsch processes include, for example, iron, cobalt, nickel, and ruthenium. While various interrelated reactions may occur in Fischer-Tropsch processes, the overall reaction process may be generally represented by Reaction [2] below.

$$(2n+1)H_2 + nCO \rightarrow C_nH_{2n+2} + nH_2O \qquad [2]$$

As mentioned above, synthesis gas may also be reacted by first performing a methanol synthesis (MS) process, and then performing a methanol-to-gasoline (MTG) process to produce liquid fuels. Methanol synthesis (MS) processes involve the catalytic conversion of carbon monoxide, carbon dioxide, hydrogen, and water to methanol and other reaction byproducts. The methanol synthesis reactions may be generally represented by Reactions [3], [4], and [5] below.

$$CO + 2H_2 \rightarrow CH_3OH \qquad [3]$$

$$CO_2 + 3H_2 \rightarrow CH_3OH + H_2O \qquad [4]$$

$$CO + H_2O \rightarrow CO_2 + H_2 \qquad [5]$$

The methanol-to-gas (MTG) process involves the conversion of methanol to hydrocarbon molecules using zeolite catalysts, which are described in further detail below. The methanol-to-gas (MTG) process occurs in two steps. First, methanol is heated to about 300° C. and partially dehydrated over an alumina catalyst at about 2.7 megapascals to yield an equilibrium mixture of methanol, dimethyl ether, and water. This effluent is then mixed with synthesis gas and introduced into a reactor containing a zeolite catalyst (such as, for example, a ZSM-5 zeolite), at temperatures between about 350° C. and about 366° C. and at pressures between about 1.9 megapascals and about 2.3 megapascals, to produce hydrocarbons and water. The methanol-to-gas (MTG) reactions may be generally represented by Reactions [6], [7], and [8] below.

$$2CH_3OH \rightarrow CH_3OCH_3 + H_2O \qquad [6]$$

$$CH_3OCH_3 \rightarrow C_2\text{-}C_5 \text{ Olefins} \qquad [7]$$

$$C_2\text{-}C_5 \text{ Olefins} \rightarrow \text{Paraffins, Cycloparaffins, Aromatics} \qquad [8]$$

While the feasibility of the above-described reactions has been demonstrated, mass production of liquid fuels using such processes has not been widely implemented due, at least in part, to the relatively high costs associated with carrying out the reactions, and to the relatively low yields exhibited by the reactions.

In an effort to improve the yield of the various reactions and to minimize the costs associated with carrying out the reactions, research has been conducted in an effort to improve the efficiency of the catalysts associated with each of the respective catalyzed reactions. As previously mentioned, zeolites have been used as catalysts in the methanol-to-gas (MTG) process.

Zeolites are substantially crystalline oxide materials in which the crystal structure of the oxide material defines pores, channels, or both pores and channels in the oxide material. Such pores and channels may have cross-sectional dimensions of between about 1 angstrom and about 200 angstroms, and typically have cross-sectional dimensions of between about 3 angstroms and about 15 angstroms. Typically, zeolite materials include metal atoms (classically, silicon or aluminum) that are surrounded by four oxygen anions to form an approximate tetrahedron consisting of a metal cation at the center of the tetrahedron and oxygen anions at the four apexes of the tetrahedron. The tetrahedral metals are often referred to as "T-atoms." These tetrahedra then stack in substantially regular arrays to form channels. There are various ways in which the tetrahedra may be stacked, and the resulting "frameworks" have been documented and categorized in, for example, Ch. Baerlocher, W. M. Meier and D. H. Olson, *Atlas of Zeolite Framework Types*, 5th ed., Elsevier: Amsterdam, 2001, the contents of which are hereby incorporated herein in their entirety by this reference.

Silicon-based tetrahedra in zeolitic materials are electrically neutral since silicon typically exhibits a 4+ oxidation state. Tetrahedra based on elements other than silicon, however, may not be electrically neutral, and charge-compensating ions may be present so as to electrically neutralize the non-neutral tetrahedra. For example, many zeolites are aluminosilicates. Aluminum typically exists in the 3+ oxidation state, and charge-compensating cations typically populate the pores to maintain electrical neutrality. These charge-compensating cations may participate in ion-exchange processes. When the charge-compensating cations are protons, the zeolite may be a relatively strong solid acid. The acidic properties of such solid acid zeolites may contribute to their catalytic properties. Other types of reactive metal cations may also populate the pores to form catalytic materials with unique properties.

Notwithstanding the research that has been conducted with respect to the above-described reactions and their respective catalytic materials, there remains a need in the art for catalytic materials and structures than can be used to provide a direct route or mechanism for the reduction of carbon monoxide (CO) and/or carbon dioxide ($CO_2$) to liquid fuels. As used herein, the term "carbon oxide" ($CO_x$) means and includes at least one of CO and $CO_2$.

BRIEF SUMMARY OF THE INVENTION

In one embodiment, the present invention includes a method of fabricating a catalytic structure that comprises forming a reaction mixture comprising a zinc salt, a copper salt, a hydroxyl ion source, and a structure-directing agent. The reaction mixture is heated under confined volume conditions to produce a precursor of a catalytic structure comprising zinc oxide and copper oxide. The zinc oxide has a sheet-like morphology or a spherical morphology. The method further comprises reducing the copper oxide to copper.

In another embodiment, the present invention includes a method of hydrogenating a carbon oxide that comprises contacting a catalytic structure with hydrogen and at least one of carbon monoxide and carbon dioxide. The catalytic structure comprises zinc oxide and copper metal. The zinc oxide has a sheet-like morphology or a spherical morphology and the copper metal comprises particles of copper metal.

In one embodiment, the present invention includes a precursor to a catalytic structure that comprises zinc oxide and copper oxide. The zinc oxide has a sheet-like morphology or a spherical morphology and the copper oxide comprises particles of copper oxide.

In another embodiment, the present invention includes a catalytic structure that comprises zinc oxide and copper metal. The zinc oxide has a sheet-like morphology or a spherical morphology and the copper metal comprises particles of copper metal.

In another embodiment, the present invention includes a system for producing an alcohol from hydrogen and at least one of carbon monoxide and carbon dioxide. The system comprises a reactor configured to receive a reactant mixture comprising hydrogen and at least one of carbon monoxide and carbon dioxide and a catalytic structure disposed within the reactor. The catalytic structure comprises zinc oxide and copper metal. The zinc oxide has a sheet-like morphology or a spherical morphology and the copper metal comprises particles of copper metal.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
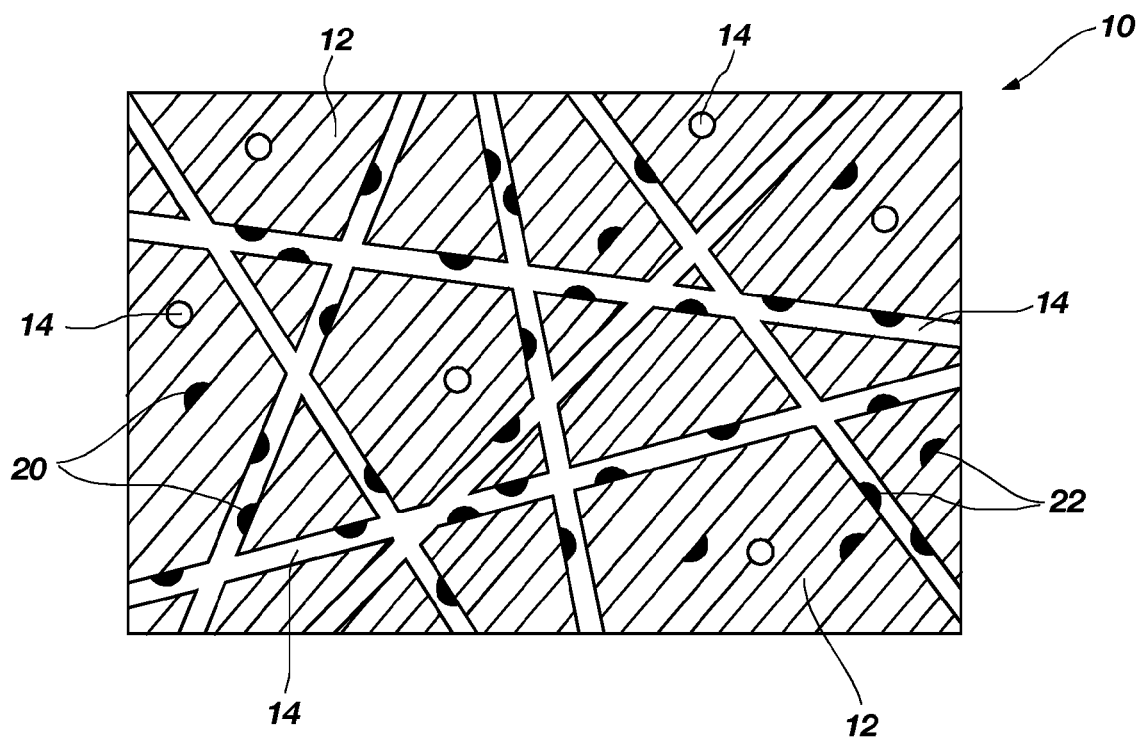
FIG. 1 is a cross-sectional view of one example of a catalytic structure that embodies teachings of the present invention and includes a metal material and a metal oxide material that are disposed within pores of a zeolite material.

As used herein, the term "zeolite material" means and includes any substantially crystalline material generally represented by the formula:

$$M_x M'_y \ldots N_z [T_m T'_n \ldots O_{2(m+n+\ldots)-\epsilon}(OH)_{2\epsilon}](OH)_{br} (Aq)_p \cdot qQ,$$

wherein M and M' represent exchangeable and/or non-exchangeable metal cations, N represents non-metallic cations (which may be removable upon heating), T and T' represent T atoms (which may be selected from, for example, beryllium, boron, aluminum, silicon, phosphorous, gallium, and germanium), O represents oxygen atoms, OH represents hydroxide ions, Aq represents chemically bonded water (or any other strongly held ligands of the T-atoms (e.g., T and T'), and Q represents sorbate molecules which may be, but are not limited to, water molecules. In the above formula, x, y, z, m, n, $\epsilon$, br, p, and q each may be any number greater than or equal to zero. In other words, if one of the components is not present in the material, then the corresponding subscript would be zero. The portion of the formula contained within the brackets provides the framework of the substantially crystalline material. The crystal structure of zeolite materials typically include a plurality of interconnected tetrahedra and have a framework density (FD) of between about 12 and about 23, wherein the framework density is defined as the number of tetrahedrally coordinated atoms (T-atoms) per 1,000 cubic angstroms. By way of example and not limitation, zeolite materials include aluminosilicate-based materials, aluminophosphate-based materials, and silicoaluminophosphate-based materials. An example of a zeolite material is an aluminosilicate-based material having a chemical structure in which the unit cell (smallest geometrically repeating unit of the crystal structure) is generally represented by the formula:

$$M_{(y/n)}[(AlO_2)_y (SiO_2)_z] \cdot (x)H_2O,$$

wherein M is a cation selected from elements in Group IA and Group IIA of the Periodic Table of the Elements (including, for example, sodium, potassium, magnesium and calcium), n is the valence of the cations M, x is the number of water molecules per unit cell, y is the number of $AlO_2$ units per unit cell, and z is the number of $SiO_2$ units per unit cell. In some zeolite materials, the ratio of z to y (z/y) may be any number greater than 1. Another example of a zeolite material is a silicoaluminophosphate-based material having a chemical structure in which the unit cell is generally represented by the formula:

$$(Si_a Al_b P_c)O_2 \cdot (x)H_2O,$$

wherein x is the number of water molecules per unit cell, z is the number of silicon atoms per unit cell, b is the number of aluminum atoms per unit cell, and c is the number of phosphorous atoms per unit cell. Such silicoaluminophosphate-based materials may also include a small amount of organic amine or quaternary ammonium templates, which are used to form the materials and retained therein. Such zeolite materials may further include additional elements and materials disposed within the interstitial spaces of the unit cell.

As used herein, the term "pore" means and includes any void in a material and includes voids of any size and shape. For example, pores include generally spherical voids, generally rectangular voids, as well as elongated voids or channels having any cross-sectional shape including nonlinear or irregular shapes.

As used herein, the term "micropore" means and includes any void in a material having an average cross-sectional dimension of less than about 20 angstroms (2 nanometers). For example, micropores include generally spherical pores having average diameters of less than about 20 angstroms, as well as elongated channels having average cross-sectional dimensions of less than about 20 angstroms.

As used herein, the term "mesopore" means and includes any void in a material having an average cross-sectional dimension of greater than about 20 angstroms (2 nanometers) and less than about 500 angstroms (50 nanometers). For example, mesopores include generally spherical pores having average diameters between about 20 angstroms and about 500 angstroms, as well as elongated channels having average cross-sectional dimensions between about 20 angstroms and about 500 angstroms.

As used herein, the term "macropore" means and includes any void in a material having an average cross-sectional dimension of greater than about 500 angstroms (50 nanometers). For example, macropores include generally spherical pores having average diameters greater than about 500 angstroms, as well as elongated channels having average cross-sectional dimensions greater than about 500 angstroms.

The illustrations presented herein are not meant to be actual views of any particular catalytic structure, reactor, or system, but are merely idealized representations which are employed to describe the present invention. Additionally, elements common between figures may retain the same numerical designation.

One example of a catalytic structure 10 that embodies teachings of the present invention is shown in FIG. 1. The catalytic structure 10 includes a zeolite material 12 that is capable of catalyzing the formation of hydrocarbon molecules having two or more carbon atoms from methanol. As discussed in further detail below, the zeolite material 12 may have both a mesoporous structure and a microporous structure.

Referring to FIG. 1, the catalytic structure 10 may include a plurality of mesopores 14 dispersed throughout the zeolite material 12. The mesopores 14 may include elongated channels extending randomly through the zeolite material 12. By way of example and not limitation, some of the mesopores 14 may include an elongated pore having a generally cylindrical shape and an average cross-sectional diameter in a range extending from about 20 angstroms (2 nanometers) to about 500 angstroms (50 nanometers). Other mesopores 14 may be generally spherical and may have an average diameter in a range extending from about 20 angstroms (2 nanometers) to about 500 angstroms (50 nanometers). In additional embodiments, the mesopores 14 may be disposed in an ordered array within the zeolite material 12. For example, the mesopores 14 may include elongated channels extending generally parallel to one another through the zeolite material 12. In some embodiments, communication may be established between at least some of the mesopores 14. In additional embodiments, each mesopore 14 may be substantially isolated from other mesopores 14 by the zeolite material 12. Furthermore, the zeolite material 12 may include a plurality of macropores in addition to, or in place of, the plurality of mesopores 14.

In one embodiment of the present invention, the zeolite material 12 may have an MFI framework type as defined in Ch. Baerlocher, W. M. Meier and D. H. Olson, *Atlas of Zeolite Framework Types*, 5th ed., Elsevier: Amsterdam, 2001. Furthermore, the zeolite material 12 may include an aluminosilicate-based material. By way of example and not limitation, the zeolite material 12 may include ZSM-5 zeolite material, which is an aluminosilicate-based zeolite material having an MFI framework type. Furthermore, the zeolite material 12 may be acidic. For example, at least some metal cations of the zeolite material 12 may be replaced with hydrogen ions to provide a desired level of acidity to the zeolite material 12. Ion exchange reactions for replacing metal cations in a zeolite material with hydrogen ions are known in the art.

Figure 2:
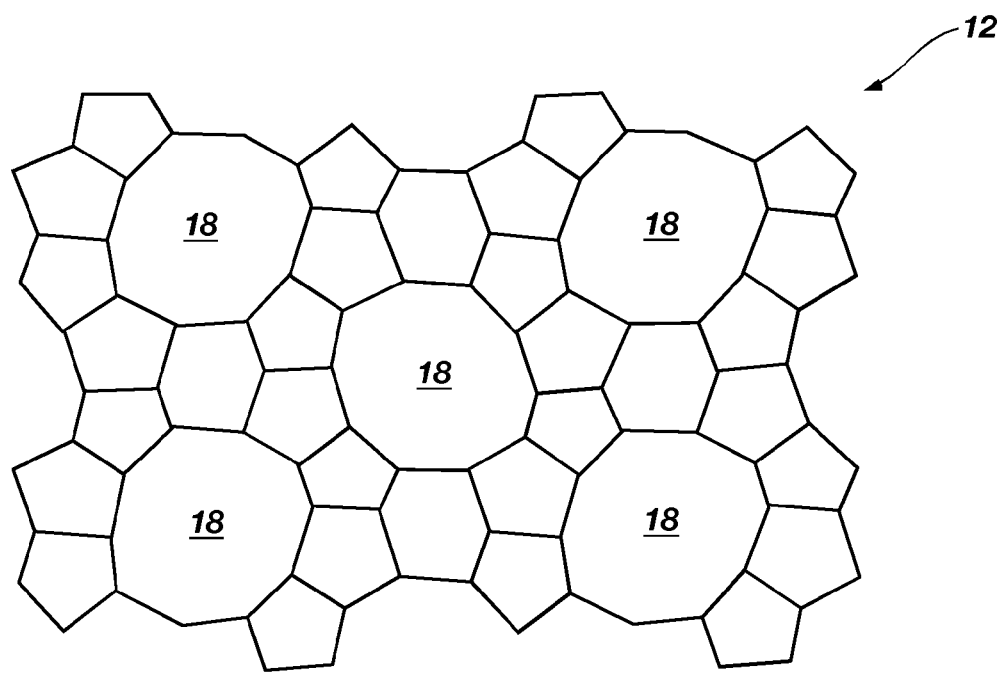
FIG. 2 is a simplified illustration representing one example of a chemical structure framework that may be exhibited by the zeolite material shown in FIG. 1.

FIG. 2 is an enlarged view of a portion of the zeolite material 12 shown in FIG. 1 and provides a simplified representation of the chemical structure framework of a zeolite material 12 having an MFI framework type, as viewed in the [010] direction. As shown therein, the zeolite material 12 may include a plurality of micropores 18 that extend through the zeolite material 12 and are substantially defined by the interstitial spaces within the crystal structure of the zeolite material 12. The micropores 18 shown in FIG. 2 may be substantially straight. The zeolite material 12 may further include additional micropores (not shown in FIG. 2) that extend through the zeolite material 12 in the [100] direction in a generally sinusoidal pattern.

Various types of zeolite materials 12 are known in the art, and any zeolite material 12 that exhibits catalytic activity with respect to the formation of hydrocarbon molecules from methanol, as discussed in further detail below, may be used in catalytic structures that embody teachings of the present invention, such as the catalytic structure 10 shown in FIG. 1. For example, the zeolite material 12 may include a silicoaluminophosphate-based material. Furthermore, the zeolite material 12 may have framework types other than MFI. By way of example and not limitation, the zeolite material 12 may have a BEA, FAU, MOR, FER, ERI, OFF, CHA or an AEI framework type. By way of example and not limitation, the zeolite material 12 may include SAPO-34 (CHA) or ALPO$_4$-18 (AEI).

Figure 3:
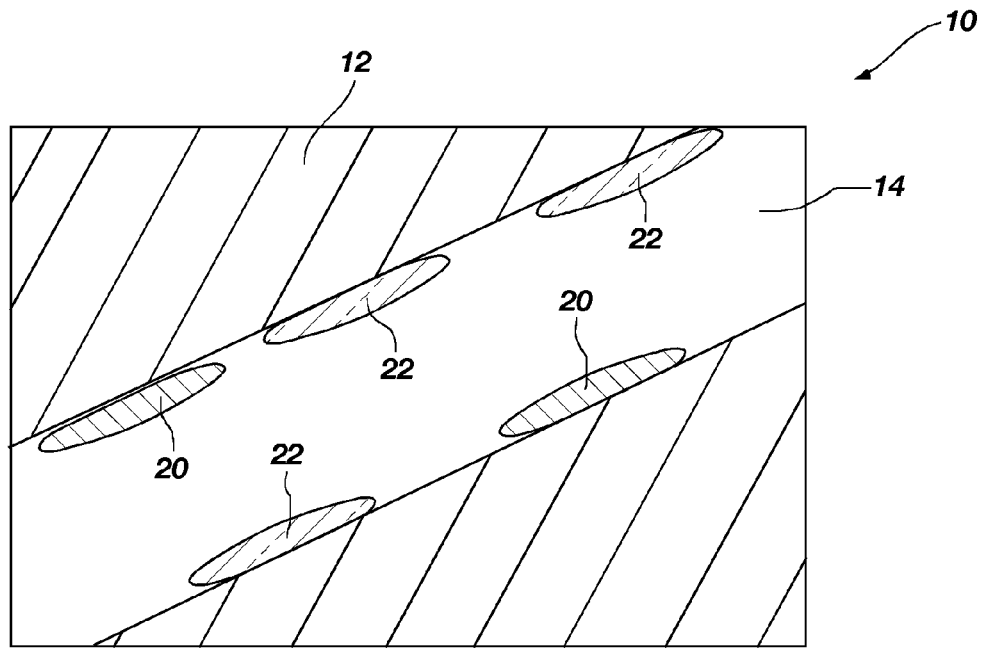
FIG. 3 is an enlarged cross-sectional view of a pore extending through the zeolite material shown in FIG. 1 and illustrating catalytic material within the pore.

Referring to FIG. 3, the catalytic structure 10 further includes an additional catalytic material disposed on and/or in the zeolite material 12. The additional catalytic material may be capable of catalyzing the formation of methanol from one or both of carbon monoxide (CO) and carbon dioxide ($CO_2$) in the presence of hydrogen. For example, the catalytic structure 10 may include a first catalytic material 20 and a second catalytic material 22 disposed on interior and/or exterior surfaces of the zeolite material 12. As shown in FIG. 3, the first catalytic material 20 and the second catalytic material 22 may be disposed within mesopores 14 of the zeolite material 12. It is contemplated that the first catalytic material 20, the second catalytic material 22, or both the first catalytic material 20 and the second catalytic material 22 also may be disposed within micropores 18 (FIG. 2) of the zeolite material 12.

In some embodiments, the first catalytic material 20 may form a coating extending over surfaces of the zeolite material 12 within the mesopores 14. In additional embodiments, the first catalytic material 20 may be configured as a plurality of nanoparticles disposed within the mesopores 14 of the zeolite material 12. Such nanoparticles may have an average diameter of, for example, less than about 500 angstroms (50 nanometers), and, more particularly, less than about 200 angstroms (20 nanometers). Similarly, the second catalytic material 22 may form a coating extending over surfaces of the zeolite material 12 within the mesopores 14. In additional embodiments, the second catalytic material 22 may be configured as a plurality of nanoparticles disposed within mesopores 14 of the zeolite material 12. Such nanoparticles may have an average diameter of, for example, less than about 500 angstroms (50 nanometers), and, more particularly, less than about 200 angstroms (20 nanometers).

In yet additional embodiments, the first catalytic material 20 and the second catalytic material 22 each may comprise regions of a single layer or coating extending over surfaces of the zeolite material 12 within the mesopores 14.

In some embodiments of the present invention, one or both of the first catalytic material 20 and the second catalytic material 22 may be chemically bound to the zeolite material 12 by, for example, a chemical complex or a chemical bond. In additional embodiments, the first catalytic material 20 and the second catalytic material 22 may be physically bound to the zeolite material 12 by mechanical interference between surfaces of the zeolite material 12 and conformal layers of one or both of the first catalytic material 20 and the second catalytic material 22 formed over such surfaces of the zeolite material 12. In yet other embodiments, there may be substantially no chemical or physical bond between the zeolite material 12 and one or both of the first catalytic material 20 and the second catalytic material 22. For example, nanoparticles of one or both of the first catalytic material 20 and the second catalytic material 22 may be generally loosely disposed within the mesopores 14 of the zeolite material 12.

As previously mentioned, the first catalytic material 20 and the second catalytic material 22 may be capable of catalyzing the formation of methanol from at least one of carbon monoxide and carbon dioxide in the presence of hydrogen. By way of example and not limitation, the first catalytic material 20 may include a metallic material such as, for example, copper, magnesium, zinc, cobalt, iron, nickel, ruthenium, platinum, palladium, or cesium (including alloys based on one or more of such metallic materials). By way of example and not limitation, the second catalytic material 22 may include a metal oxide material such as, for example, zinc oxide, magnesium oxide, zirconium oxide, iron oxide, or tungsten oxide.

One example of a method that may be used to form catalytic structures that embody teachings of the present invention, such as, for example, the catalytic structure 10 shown in FIGS. 1-3, will now be described with reference to FIGS. 4-7.

Figure 4:
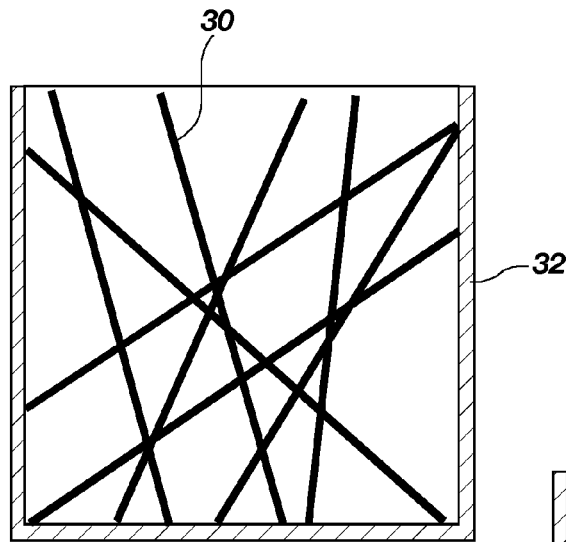
FIGS. 4-7 illustrate one example of a method that may be used to fabricate a catalytic structure according to teachings of the present invention.

Referring to FIG. 4, a plurality of template structures 30 may be provided within a container 32. The template structures 30 may have a selected size and shape corresponding to a desired size and shape of pores, such as, for example, the mesopores 14 (FIG. 1), to be formed in the catalytic structure 10. By way of example and not limitation, the template structures 30 may comprise nanoparticles, nanowires, or nanotubes. The template structures 30 may be formed from or include any material that may be subsequently removed from a zeolite material 12 formed around the template structures 30 without significantly damaging or otherwise affecting the zeolite material 12. By way of example and not limitation, the template structures 30 may include carbon. In the embodiment shown in FIG. 4, the template structures 30 include carbon nanowires. Each carbon nanowire may be generally cylindrical and may have an average cross-sectional diameter between about 10 angstroms (1 nanometer) and about 2,000 angstroms (200 nanometers).

In additional embodiments, the template structures 30 may include carbon nanoparticles, carbon nanotubes, or a mixture of at least two of carbon nanowires, nanoparticles, and nanotubes. Furthermore, the template structures 30 optionally may be formed from or include materials other than carbon such as, for example, any polymer material allowing the formation of a zeolite material 12 around the template structures 30 and subsequent removal of the polymer material from the zeolite material 12 without significantly damaging or otherwise affecting the zeolite material 12.

Figure 5:
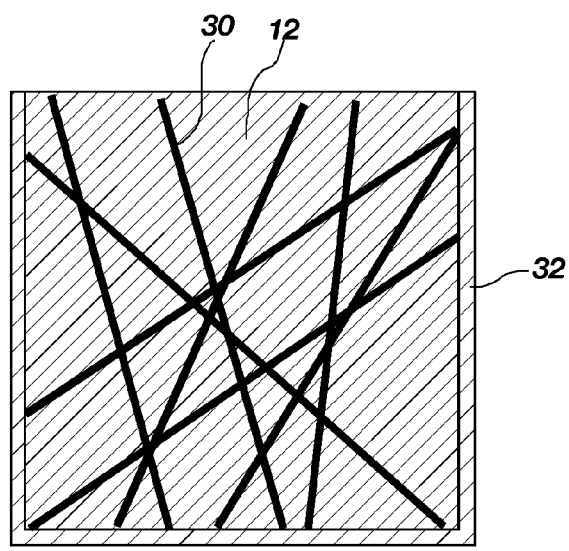

Referring to FIG. 5, a zeolite material 12 may be formed around the template structures 30 using methods known in the art, such as, for example, those methods described in U.S. Pat. No. 3,702,886 to Argauer et al., the entire disclosure of which is incorporated herein in its entirety by this reference.

Figure 6:
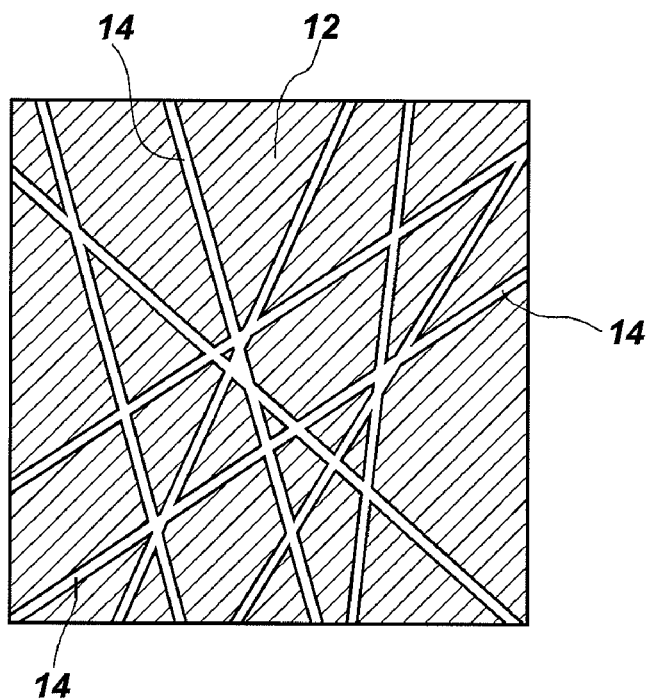

After forming the zeolite material 12 around the template structures 30, the template structures 30 may be removed from within the zeolite material 12 to form mesopores 14 (and optionally macropores), as shown in FIG. 6. If the template structures 30 comprise carbon material, the carbon material may be removed by, for example, calcining in air. By way of example and not limitation, the zeolite material 12 and the template structures 30 may be heated in air to temperatures of about 600° C. for about twenty hours to calcine the carbon material.

After removing the template structures 30 from within the zeolite material 12 to form the mesopores 14 (and optionally macropores), the first catalytic material 20 and the second catalytic material 22 may be provided on and/or in the zeolite material 12.

By way of example and not limitation, particles of the first catalytic material 20 and particles of the second catalytic material 22 (or precursor materials from which the first catalytic material 20 and the second catalytic material 22 can be subsequently formed) may be suspended in a liquid. The liquid and the particles of the first catalytic material 20 and the second catalytic material 22 may be provided within the mesopores 14 of the zeolite material 12 by, for example, immersing the zeolite material 12 in the liquid suspension. The zeolite material 12 then may be removed from the liquid suspension and allowed to dry (at ambient or elevated temperatures) to remove the liquid from the liquid suspension, leaving behind the particles of the first catalytic material 20 and the second catalytic material 22 within the mesopores 14 of the zeolite material 12.

As another example, the first catalytic material 20 and the second catalytic material 22 may be provided on and/or in the zeolite material 12 by precipitation of their respective metal salts (i.e., nitrates or acetates). The precursor salts may be provided in the mesopores 14 of the zeolite material 12 using, for example, the incipient wetness technique. The precursor salts then may be precipitated using standard reagents such as, for example, ammonia or sodium hydroxide. As previously discussed herein, in one embodiment of the present invention, the first catalytic material 20 may include copper and the second catalytic material 22 may include zinc oxide. One method by which copper and zinc oxide may be provided within mesopores 14 of the zeolite material 12 is to immerse the zeolite material 12 in a nitrate solution comprising copper nitrate ($Cu(NO_3)_2$) and zinc nitrate ($Zn(NO_3)_2$). In additional embodiments, the zeolite material 12 may be first immersed in one of a copper nitrate solution and a zinc nitrate solution, and subsequently immersed in the other of the copper nitrate solution and the zinc nitrate solution. Furthermore, the zeolite material 12 may be dried after immersion in the first nitrate solution and prior to immersion in the second nitrate solution.

The copper nitrate and zinc nitrate on and within the zeolite material 12 then may converted to copper oxide (CuO) and zinc oxide (ZnO) by, for example, heating the zeolite material 12 in air to temperatures between about 100° C. and about 250° C. The copper oxide (CuO) then may be converted to copper (Cu) by, for example, flowing hydrogen gas ($H_2$) over the zeolite material 12 at elevated temperatures (for example, about 240° C.).

As yet another example, the first catalytic material 20 and the second catalytic material 22 may be provided on and/or in the zeolite material 12 by preparing a first aqueous solution of zinc nitrate and copper nitrate and adding the zeolite material 12 to the aqueous solution. An additional solution may be prepared that includes hexamethylenetetramine and sodium citrate. This additional solution may be added to the first aqueous solution, and the mixture may be heated in a closed vessel, such as, for example, a Parr acid digestion bomb, to between about 95° C. and about 120° C. for between about one hour and about four hours. The sample then may be filtered, washed, and dried. The sample then may be oxidized in air at temperatures between about 100° C. and about 250° C. to form the copper oxide and zinc oxide, after which the copper oxide may be converted to copper as described above. The reaction for providing the first catalytic material 20 and the second catalytic material 22 on and/or in the zeolite material 12 is a hydrothermal reaction. As used herein, the term "hydrothermal reaction" means and includes the synthesis of an amorphous or crystalline form of the catalytic structure 10 from high-temperature aqueous solutions at a high vapor pressure.

In an additional method that embodies teachings of the present invention, the template structures 30 shown in FIG. 4 may include carbon nanotubes. The carbon nanotubes may be impregnated with a solution comprising copper nitrate and zinc nitrate. After forming the zeolite material 12 around the impregnated carbon nanotubes, the carbon nanotubes may be removed by calcining in air, as previously described, and copper and zinc oxide may be formed from the copper nitrate and the zinc nitrate, respectively, as the carbon nanotubes are calcined in the air.

Figure 7:
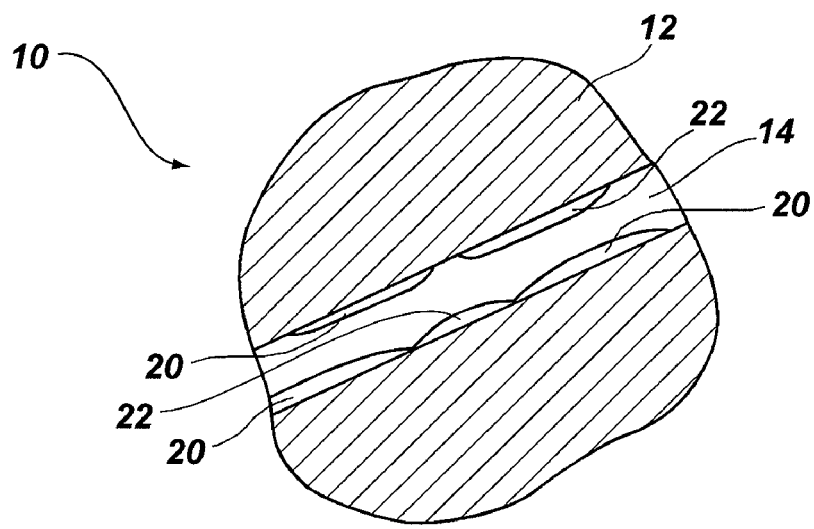

Referring to FIG. 7, the above described method may be used to provide the first catalytic material 20, which may include copper (Cu), and the second catalytic material 22, which may include zinc oxide (ZnO), within mesopores 14 of the zeolite material 12 (and optionally within micropores 18 and/or macropores of the zeolite material 12) and to form the catalytic structure 10.

Figure 8:
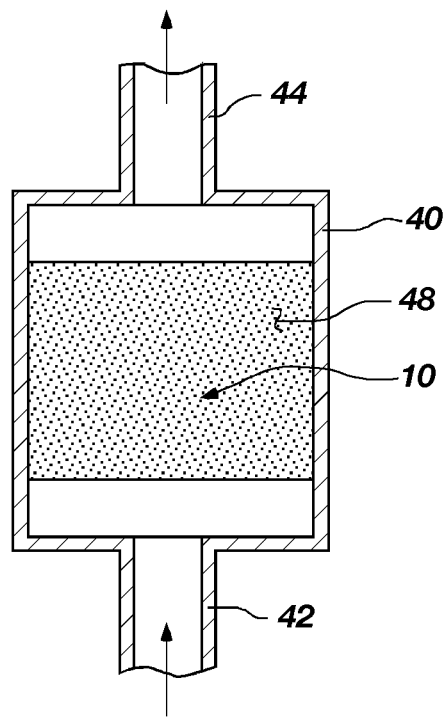
FIG. 8 is a partial cross-sectional view of a reactor that includes a catalytic structure that embodies teachings of the present invention.

Referring to FIG. 8, in some embodiments of the present invention, the catalytic structure 10 may include a quantity of powder 48 comprising relatively fine particles. The particles of the powder 48 may include first and second catalytic materials 20, 22 disposed within a zeolite material 12, as previously described in relation to FIGS. 1-3. The powder 48 may be provided within a container (i.e., a reactor) 40 having an inlet 42 and an outlet 44, and the powder 48 may be disposed between the inlet 42 and the outlet 44. In this configuration, a gas comprising hydrogen and at least one of carbon monoxide (CO) and carbon dioxide ($CO_2$) may be introduced into the container 40 through the inlet 42. As the gas contacts the powder 48, the powder 48 may catalyze the formation of hydrocarbon molecules having two or more carbon atoms from the carbon monoxide (CO) and carbon dioxide ($CO_2$). In particular, the first catalytic material 20 and the second catalytic material 22 (FIG. 3) may catalyze the formation of methanol from the carbon monoxide (CO) and carbon dioxide ($CO_2$), and the zeolite material 12 may catalyze the formation of hydrocarbon molecules having two or more carbon atoms from the methanol. The hydrocarbon molecules may be collected from the outlet 44 of the container 40 and purified and/or concentrated as necessary or desired.

Figure 9:
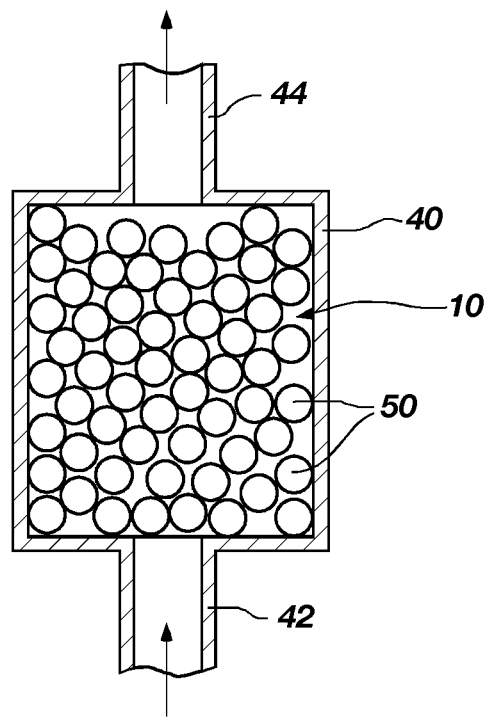
FIG. 9 is a partial cross-sectional view of a reactor that includes another catalytic structure that embodies teachings of the present invention.

Referring to FIG. 9, in additional embodiments of the present invention, the catalytic structure 10 may include a plurality of particles, briquettes, or pellets 50, each of which includes first and second catalytic materials 20, 22 disposed within a zeolite material 12, as previously described in relation to FIGS. 1-3. By way of example and not limitation, the pellets 50 may be formed by pressing the powder 48 previously described in relation to FIG. 8 in a die or mold to form the pellets 50. The plurality of pellets 50 may be provided within a container 40, as shown in FIG. 9. In this configuration, a gas comprising at least one of carbon monoxide (CO) and carbon dioxide ($CO_2$) may be introduced into the container 40 through the inlet 42, and the pellets 50 may catalyze the formation of hydrocarbon molecules having two or more carbon atoms from hydrogen and the carbon monoxide (CO) and/or carbon dioxide ($CO_2$), as previously described in relation to FIG. 8.

Figure 10:
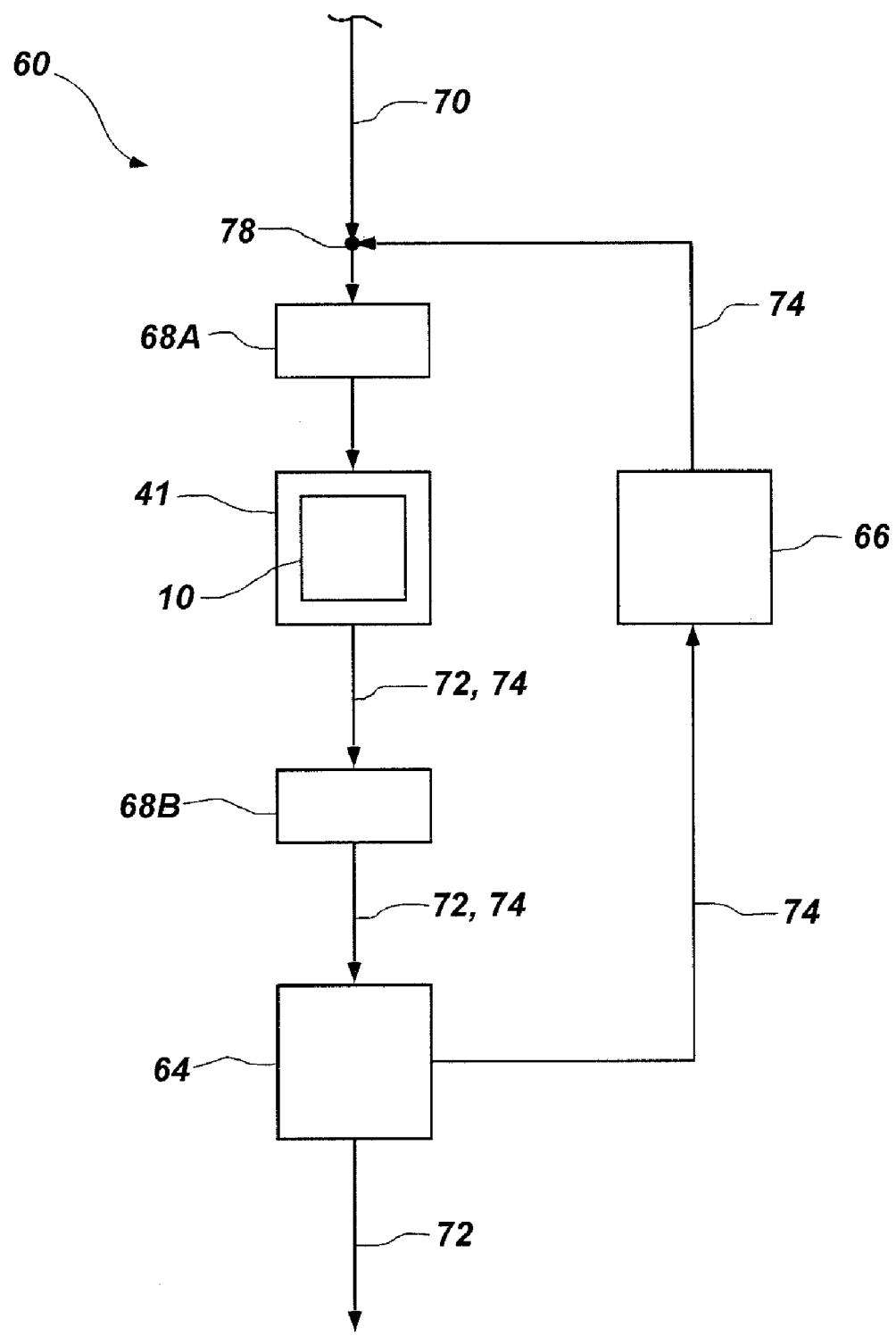
FIG. 10 is a schematic diagram of a system that embodies teachings of the present invention and includes a catalytic structure for catalyzing the formation of hydrocarbon molecules from hydrogen and at least one of carbon monoxide and carbon dioxide.

FIG. 10 is a simplified schematic of a system 60 that embodies teachings of the present invention and that may be used to form hydrocarbon molecules having two or more carbon atoms from carbon monoxide (CO) and/or carbon dioxide ($CO_2$) in the presence of hydrogen using a catalytic structure that embodies teachings of the present invention, such as, for example, the catalytic structure 10 previously described in relation to FIGS. 1-3. By way of example and not limitation, the system 60 may include a container 40, a gas-liquid separator 64, and a compressor 66. As previously discussed, the container 40 may include a catalytic structure that embodies teachings of the present invention, such as, for example, the catalytic structure 10. The system 60 may further include a first heat exchanger 68A for heating a reactant mixture fed to the container 40, and a second heat exchanger 68B for cooling products (and any unreacted reactants and/or reaction byproducts) as they exit the container 40.

The system 60 may further include a heating device (not shown) for heating the container 40 and the catalytic structure 10 to elevated temperatures. For example, a heating device may be configured to heat the container 40 and the catalytic structure 10 to a temperature between about 200° C. and about 500° C. Furthermore, the container 40 may be pressurized to between about 0.5 megapascals (5 atmospheres) and about 10 megapascals (100 atmospheres).

As shown in FIG. 10, a reactant mixture 70 that includes $H_2$ and at least one of carbon monoxide (CO) and carbon dioxide ($CO_2$) may be passed through the first heat exchanger 68A and fed to the container 40. The $CO_x$ may be a feedstock obtained from a fermentation process, a combustion process, a coal-powered or hydrocarbon-powered electricity generation plant, a natural gas reforming process, a by product of cement manufacture, the partial oxidation of biomass, or the partial oxidation of coal. The $H_2$ may be a feedstock obtained from a renewable energy source process, such as a wind energy process, a solar process, a geothermal process, the partial oxidation of biomass, or a water-splitting process. Alternatively, the $H_2$ may be a feedstock obtained from a non-renewable energy source process, such as natural gas, steam reforming, hydrocarbon reforming, or the partial oxidation of coal. As previously discussed, the catalytic structure 10 may catalyze the formation of hydrocarbon molecules having two or more carbon atoms from the hydrogen and carbon monoxide (CO) and/or carbon dioxide ($CO_2$). A product mixture 72 (which may include such hydrocarbon molecules), together with any unreacted reactant gases 74 and reaction byproducts, may be collected from the container 40 and passed through the second heat exchanger 68B to the gas-liquid separator 64. The gas liquid separator 64 may be used to separate liquid hydrocarbon products of the product mixture 72 from the unreacted reactant gases 74. The unreacted reactant gasses 74 may be re-pressurized as necessary using the compressor 66 and recombined with the reactant mixture 70 through the three-way valve 78, as shown in FIG. 10.

The liquid hydrocarbon products in the product mixture 72 collected from the gas-liquid separator 64 may then be further processed as necessary or desired. For example, additional distillation equipment (not shown) may be used to purify and concentrate the various hydrocarbon components in the product mixture 72 as necessary or desired.

The catalytic structures, systems, and methods described herein may be used to catalyze the conversion of hydrogen and at least one of carbon monoxide and carbon dioxide to hydrocarbons having two or more carbon atoms with improved catalytic activity and selectivity relative to known catalytic structures, systems, and methods. Furthermore, the catalytic structures, systems, and methods described herein may facilitate economic utilization of carbon dioxide from stationary carbon dioxide sources, such as coal-powered and hydrocarbon-powered electricity generation plants, which otherwise may be vented to the atmosphere. Furthermore, the methods described herein may be used to fabricate various catalytic structures, other than those described herein, that include a bi-modal (microporous and mesoporous) or multi-modal (microporous, mesoporous, and macroporous) zeolite material and a metal and/or metal oxide catalyst material disposed on and/or in the zeolite material. Such catalytic structures may be bi-functional. In other words, the zeolite material itself may function as one catalytic material, while the catalytic material disposed on and/or in the zeolite material may function as a second catalytic material. In addition to the synthesis of hydrocarbon molecules from hydrogen and carbon monoxide and/or carbon dioxide, such bi-functional catalytic structures may be useful in many additional applications where it is necessary or desirable to provide different catalytic functions to a single catalytic structure or material.

In another embodiment, a hydrothermal reaction may be used to produce a catalytic structure 10' that includes the first catalytic material 20 and the second catalytic material 22, with no additional support material. In other words, the catalytic structure 10' lacks zeolite material 12 or other support material. The catalytic structure 10' may be capable of hydrogenating a $CO_x$ to an alcohol, such as methanol, as generally represented in Reactions [3] and [4]. In one embodiment, the first catalytic material 20 is Cu and the second catalytic material 22 is ZnO, producing a copper/zinc oxide ("Cu/ZnO") catalyst as the catalytic structure 10'. The hydrothermal reaction for producing the catalytic structure 10' may be relatively inexpensive and easily scalable to produce small or large quantities of the catalytic structure 10'.

To produce the catalytic structure 10', a reaction mixture that includes a zinc salt, a copper salt, a hydroxyl ion source, and a surface-directing agent in solution may be heated in a closed vessel. A solution that includes the zinc salt and the copper salt may be prepared and combined with a solution that includes the hydroxyl ion source and the surface-directing agent. The solutions may be combined in any order. Alternatively, separate solutions of the copper salt, the zinc salt, the hydroxyl ion source, and the structure-directing agent may be prepared and combined in any order. The concentration of the copper salt in the solution may be between about 0.01 M and about 1 M and the concentration of the zinc salt in the solution may be between about 0.01 M and about 1 M. The concentration of the hydroxyl ion source in the solution may be between about 0.02 M and about 2 M and the concentration of the surface-directing agent in the solution may be between about 0.05 mM and about 0.5 M.

For the sake of example only, a third aqueous solution that includes the zinc salt and the copper salt may be combined with a fourth aqueous solution that includes the hydroxyl ion source and the structure-directing agent. Any zinc salt or copper salt that is soluble in water at the pressure conditions of the hydrothermal reaction may be used in the third aqueous solution. For the sake of example only, the zinc salt may be a zinc alkoxide, zinc acetate ($Zn(CH_3COO)_2$), zinc carbonate, zinc carbonate hydroxide, zinc citrate, zinc lactate, zinc nitrate ($Zn(NO_3)_2$), zinc oxalate, zinc stearate, zinc sulfate, or combinations thereof. For the sake of example only, the copper salt may be copper acetate, copper acetate monohydrate, copper acetate hydrate, copper carbonate, copper formate hydrate, copper gluconate, copper hydroxide, copper methoxide, copper nitrate ($Cu(NO_3)_2$), copper nitrate hydrate, copper tartrate hydrate, or combinations thereof. In one embodiment, the zinc salt is zinc nitrate and the copper salt is copper nitrate. In one embodiment, the third aqueous solution includes about 0.2 M of the copper salt and 0.2 M of the zinc salt.

The hydroxyl ion source in the fourth aqueous solution may be a source of hydroxyl ions ($OH^-$) and may provide a slow, steady supply of the $OH^-$ ions during the hydrothermal reaction. The hydroxyl ion source may be an amine including, but not limited to, hexamethylenetetramine ("HMTA"), ammonium hydroxide, ethylene diamine, triethanolamine, ammonia, hydrazine, or combinations thereof. The structure-directing agent may be sodium citrate, potassium citrate, citric acid, poly(vinyl alcohol), poly(vinyl pyrrolidone), or combinations thereof. The concentration of the HMTA in the solution may be between about 0.02 M and about 2 M and the concentration of the sodium citrate in the solution may be between about 0.05 mM and about 0.5 M. In one embodiment, the hydroxyl ion source is HMTA and the surface-directing agent is sodium citrate. In one embodiment, the fourth aqueous solution includes about 0.4 M HMTA and about 0.74 mM sodium citrate.

The fourth aqueous solution may be combined with the third aqueous solution, and the mixture heated in a closed vessel, such as in an autoclave. For the sake of example only, the vessel may be a Parr acid digestion bomb, which is a pressurized vessel lined with TEFLON® non-stick coating. During the hydrothermal reaction, the contents of the vessel may be heated to a temperature between about 80° C. and about 200° C., such as between about 95° C. and 120° C. In one embodiment, the contents of the vessel are heated to about 115° C. The contents of the vessel may be heated for an amount of time sufficient to produce a desired yield of the ZnO, such as a time ranging between about one hour and about four hours. The yield of the ZnO in the Cu/ZnO catalyst is dependent on the synthesis time. In one embodiment, the synthesis time is about three and one-half (3.5) hours.

The synthesis time may also affect the morphology of the ZnO. The ZnO may form as spherical agglomerates or as plate-like or sheet-like structures. Without being bound by a particular theory, it is believed that longer synthesis times within the above-mentioned range produce sheet-like structures of ZnO while shorter synthesis times within the above-mentioned range produce the ZnO as spherical agglomerates or nanoparticles. The morphology of the ZnO may affect the activity and selectivity of the catalytic structure 10'.

Since the mixture is heated in a closed vessel, the pressure within the vessel may depend on the temperature to which the vessel is heated. For the sake of example only, the pressure within the vessel may range between about 15 pounds per square inch ("psi") (about 0.103 megapascal) and about 25 psi (about 0.172 megapascal), such as about 20 psi (about 0.138 megapascal). The $OH^-$ ions in the fourth aqueous solution may react with the zinc salt and the copper salt to produce a mixture of zinc- and copper-containing precipitates that includes ZnO and CuO. The mixture of zinc- and copper-containing precipitates is a precursor of the Cu/ZnO catalyst. The mixture of zinc- and copper-containing precipitates may include at least one of amorphous and crystalline forms of the ZnO and CuO. The mixture of zinc- and copper-containing precipitates may be dried in air at a temperature between about 80° C. and about 550° C. The drying may initially be conducted at a lower temperature within the above-mentioned range, followed by additional drying at a higher temperature within the above-mentioned range. Drying at the lower temperature may be used to remove water from the mixture of zinc- and copper-containing precipitates, while the higher temperature drying may remove waters of hydration and convert oxy- or hydroxyl-species to CuO and ZnO (calcination). The length of the drying time may also affect the morphology of the ZnO.

Alternatively, the precursor of the Cu/ZnO catalyst may be formed in a sequential manner by combining a fifth aqueous solution that includes either the copper salt or the zinc salt with the fourth aqueous solution. The $OH^-$ ions in the fourth aqueous solution react with the copper salt (or the zinc salt) to produce CuO (or ZnO). The CuO (or ZnO) may be dried at a temperature within the range mentioned above and combined with a sixth aqueous solution that includes the opposite salt, either the zinc salt or the copper salt, and the fourth aqueous solution. The $OH^-$ ions in the fourth aqueous solution react with the zinc salt (or the copper salt), producing the precursor of the Cu/ZnO catalyst, which is dried as described above. For the sake of example only, if the fifth aqueous solution includes the copper salt, the sixth aqueous solution includes the zinc salt. Conversely, if the fifth aqueous solution includes the zinc salt, the sixth aqueous solution includes the copper salt.

The CuO in the precursor of the Cu/ZnO catalyst may be reduced to copper metal (elemental copper) by, for example, flowing $H_2$, argon (Ar) and $H_2$, or $H_2$ and nitrogen gas ($N_2$) over the ZnO and CuO at an elevated temperature, producing the active Cu/ZnO catalyst. The reduction of CuO to Cu metal may be conducted at a temperature between about 100° C. and about 270° C.

The selectivity and activity of the Cu/ZnO catalyst may depend on the relative amounts of Cu and ZnO in the Cu/ZnO catalyst, which depends on the relative amounts of CuO and ZnO in the precursor of the Cu/ZnO catalyst. The precursor of the Cu/ZnO catalyst may include between about 10% by weight ("wt %") and about 90 wt % of CuO and between about 10 wt % and about 90 wt % of ZnO. In one embodiment, the precursor of the Cu/ZnO catalyst includes about 50 wt % of CuO and about 50 wt % of ZnO. The ratio of CuO to ZnO in the precursor of the Cu/ZnO catalyst may be altered by varying the relative amounts of the copper salt and the zinc salt used during the hydrothermal reaction. The Cu/ZnO catalyst may include between about 10 wt % and about 90 wt % of Cu and between about 10 wt % and about 90 wt % of ZnO. By adjusting the ratio of Cu to ZnO, the selectivity and activity of the Cu/ZnO catalyst may be tailored as desired.

The Cu/ZnO catalyst prepared by the hydrothermal reaction may have higher catalytic activity to an alcohol than a commercially available catalyst. Since the catalytic structure 10' does not include a support material, which typically provides minimal catalytic activity, substantially all of the Cu/ZnO catalyst is formed from Cu and ZnO. Therefore, substantially all of the Cu/ZnO catalyst may provide catalytic activity and a high surface area. Since the Cu/ZnO catalyst has increased catalytic activity, the Cu/ZnO catalyst may be used to catalyze a desired reaction at a lower temperature.

To further improve the selectivity of the Cu/ZnO catalyst, at least one promoter may be present in and/or on the Cu/ZnO catalyst. The promoter may be an alkali metal, such as lithium, sodium, potassium, rubidium, cesium, or francium. To incorporate the promoter into the Cu/ZnO catalyst, an aqueous solution of an alkali metal salt may be produced. The alkali metal salt may be a water-soluble salt of the alkali metal. For the sake of example only, if cesium is to be used, the alkali metal salt may be cesium formate. The aqueous solution of the alkali metal salt may be combined with the precursor of the Cu/ZnO catalyst. After drying in air at a temperature within the range mentioned above, the promoter may be present in the precursor of the Cu/ZnO catalyst. Alternatively, the aqueous solution of the alkali metal salt may be combined with the reaction mixture before the hydrothermal synthesis. The CuO and the ZnO in the precursor of the Cu/ZnO catalyst may be subjected to a reducing environment, as described above, producing the Cu/ZnO catalyst having the promoter.

The Cu/ZnO catalyst may also include a second catalytic material present in and/or on the Cu/ZnO catalyst. The second catalytic material may be a metal oxide, such as cobalt oxide ($Co_3O_4$), chromium oxide ($Cr_2O_3$), or combinations thereof. To incorporate the second catalytic material into the Cu/ZnO catalyst, an aqueous solution of the metal oxide may be produced. This aqueous solution of the metal oxide may be combined with the precursor of the Cu/ZnO catalyst. After drying in air at a temperature within the range mentioned above, the second catalytic material may be present in the precursor of the Cu/ZnO catalyst. Alternatively, the aqueous solution of the metal oxide may be combined with the reaction mixture before the hydrothermal synthesis. The CuO and the ZnO in the precursor of the Cu/ZnO catalyst may be subjected to a reducing environment, as described above, producing the Cu/ZnO catalyst having the second catalytic material. The Cu/ZnO catalyst may also include at least one second catalytic material and at least one promoter.

Figure 11:
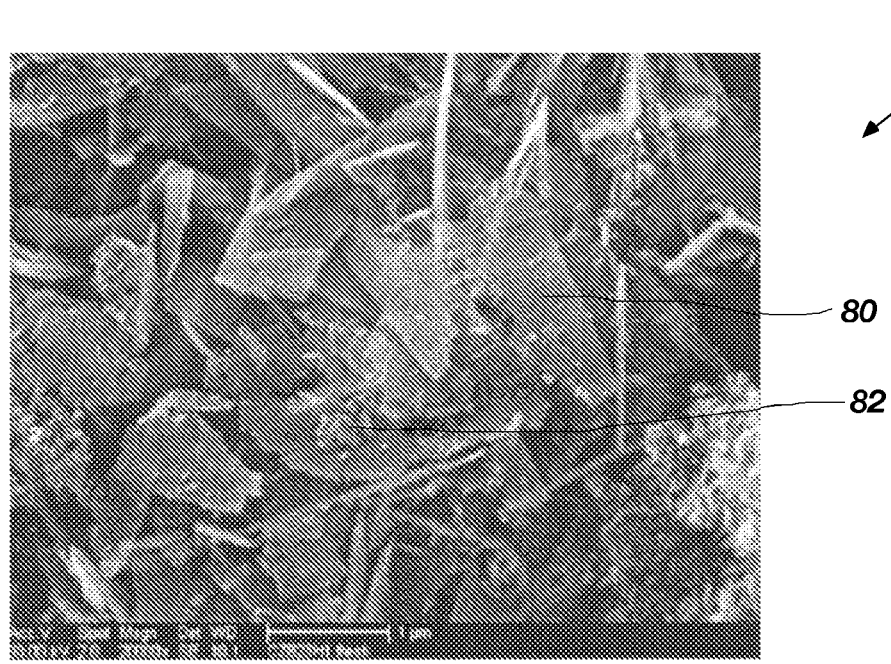
FIG. 11 is a scanning electron microscopy (SEM) photograph of a precursor of a catalytic structure that embodies teachings of the present invention and includes copper oxide and zinc oxide.
Figure 12:
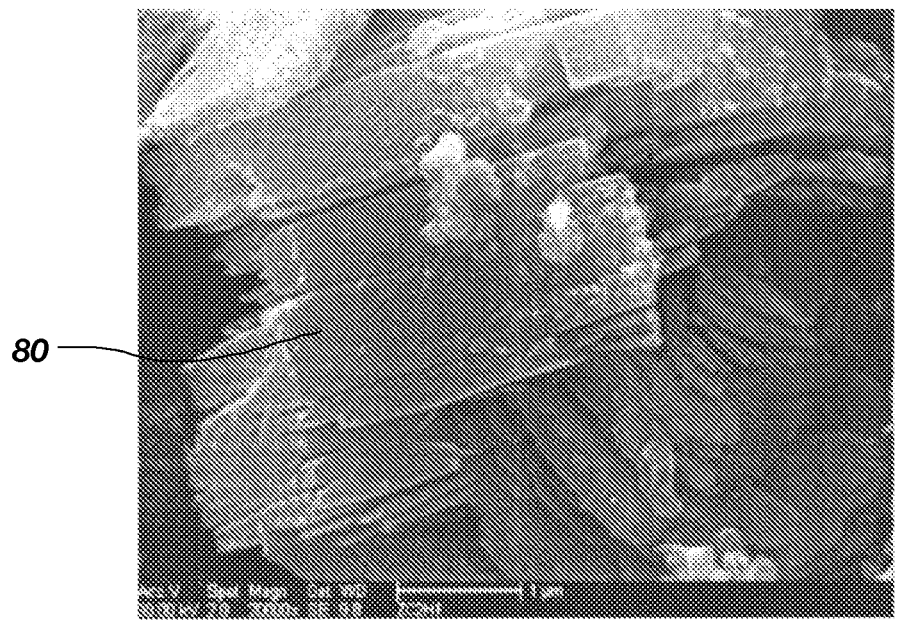
FIG. 12 is an SEM photograph illustrating a sheet-like morphology of zinc oxide.
Figure 13:
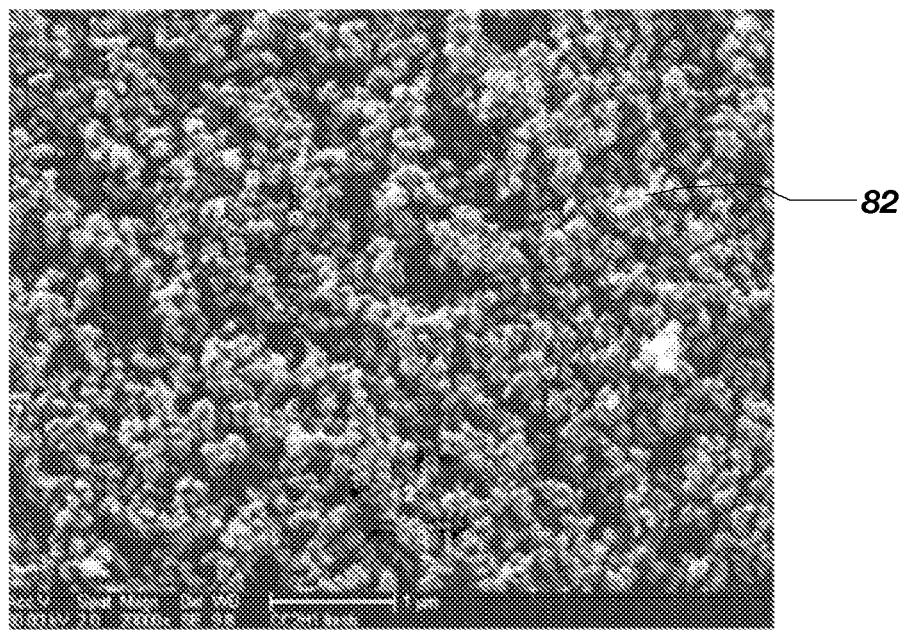
FIG. 13 is an SEM photograph illustrating copper oxide particles.
Figure 14:
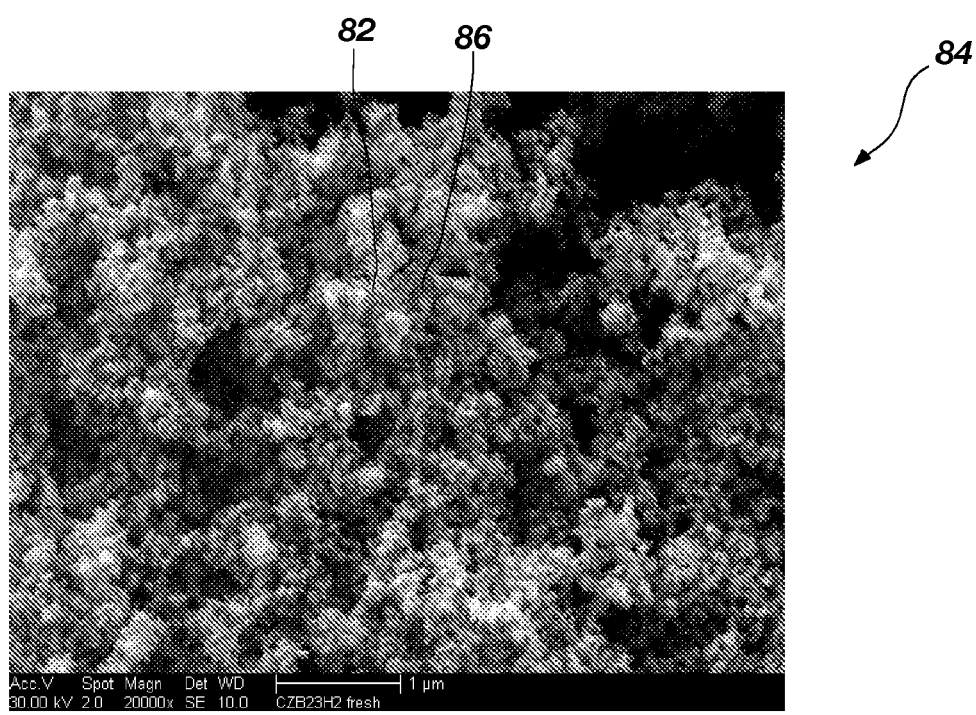
FIG. 14 is an SEM photograph of a precursor of a catalytic structure that embodies teachings of the present invention and includes copper oxide and zinc oxide.
Figure 15:
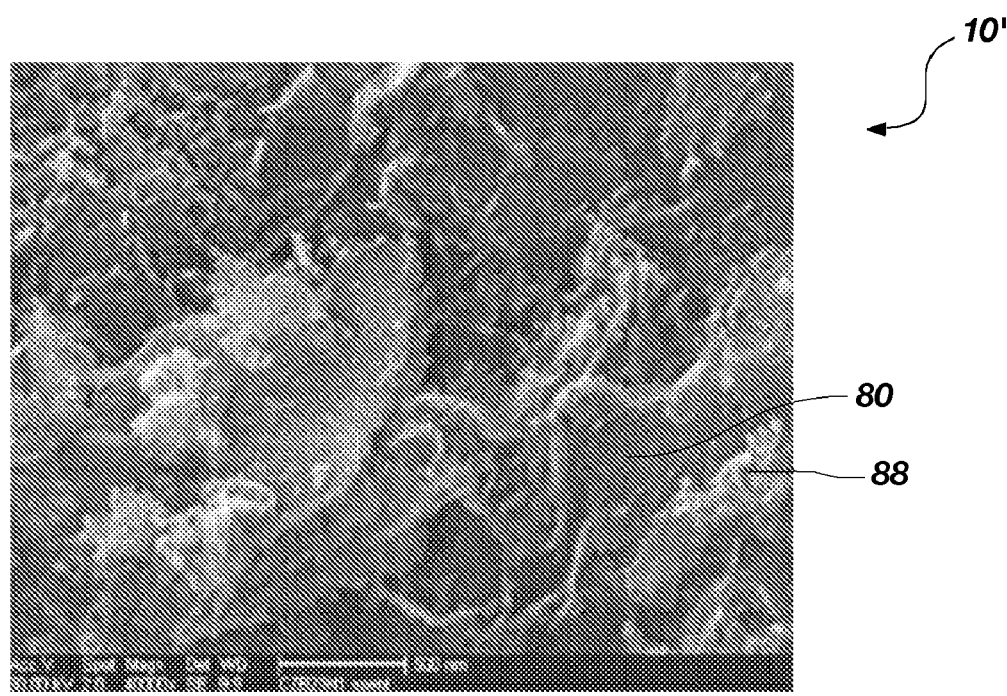
FIG. 15 is an SEM photograph of a catalytic structure that embodies teachings of the present invention and includes copper and zinc oxide.

The ZnO may provide support to the CuO in the precursor of the Cu/ZnO catalyst. Similarly, the ZnO in the Cu/ZnO catalyst may provide support to the Cu in the Cu/ZnO catalyst. As such, no additional support material is present in the precursor of the Cu/ZnO catalyst or in the Cu/ZnO catalyst. As a result of the hydrothermal synthesis, the ZnO may form plate-like or sheet-like structures 80 onto which particles 82 of the CuO are dispersed, as shown in FIG. 11, which is an SEM photograph of the precursor 84 of the Cu/ZnO catalyst. Sheet-like structures 80 of ZnO are also illustrated in FIG. 12 and particles 82 of CuO are illustrated in FIG. 13. The particles 82 may be nanoparticles having an average particle size of less than about 100 nm. Alternatively, the precursor 84 of the Cu/ZnO catalyst may include spherical structures 86 of the ZnO, which are dispersed with particles 82 of the CuO, as shown in FIG. 14. The Cu/ZnO catalyst 10' may include the sheet-like structures 80 of ZnO and particles 88 of Cu dispersed on the sheet-like structures 80, as illustrated in FIG. 15. If the ZnO has a spherical morphology, the Cu/ZnO catalyst 10' may appear substantially similar to the precursor 84 illustrated in FIG. 14, except that particles 88 of Cu are present rather than particles 82 of CuO. As previously described, the morphology of the ZnO in the precursor 84 and, therefore, in the Cu/ZnO catalyst 10' may depend on the synthesis time of the hydrothermal reaction and the drying time.

As previously mentioned, the catalytic structure 10' may be used to hydrogenate the $CO_x$ to the alcohol in the presence of hydrogen. The $CO_x$ may be CO or $CO_2$. The alcohol produced by the reaction may be methanol, ethanol, propanol, butanol, or combinations thereof. In one embodiment, methanol is produced according to Reactions [3] and [4]. The alcohol produced by the reaction may also include trace amounts of higher alcohols. The catalytic structure 10' may also be used to produce other oxygenates, such as dimethyl ether.

Figure 16:
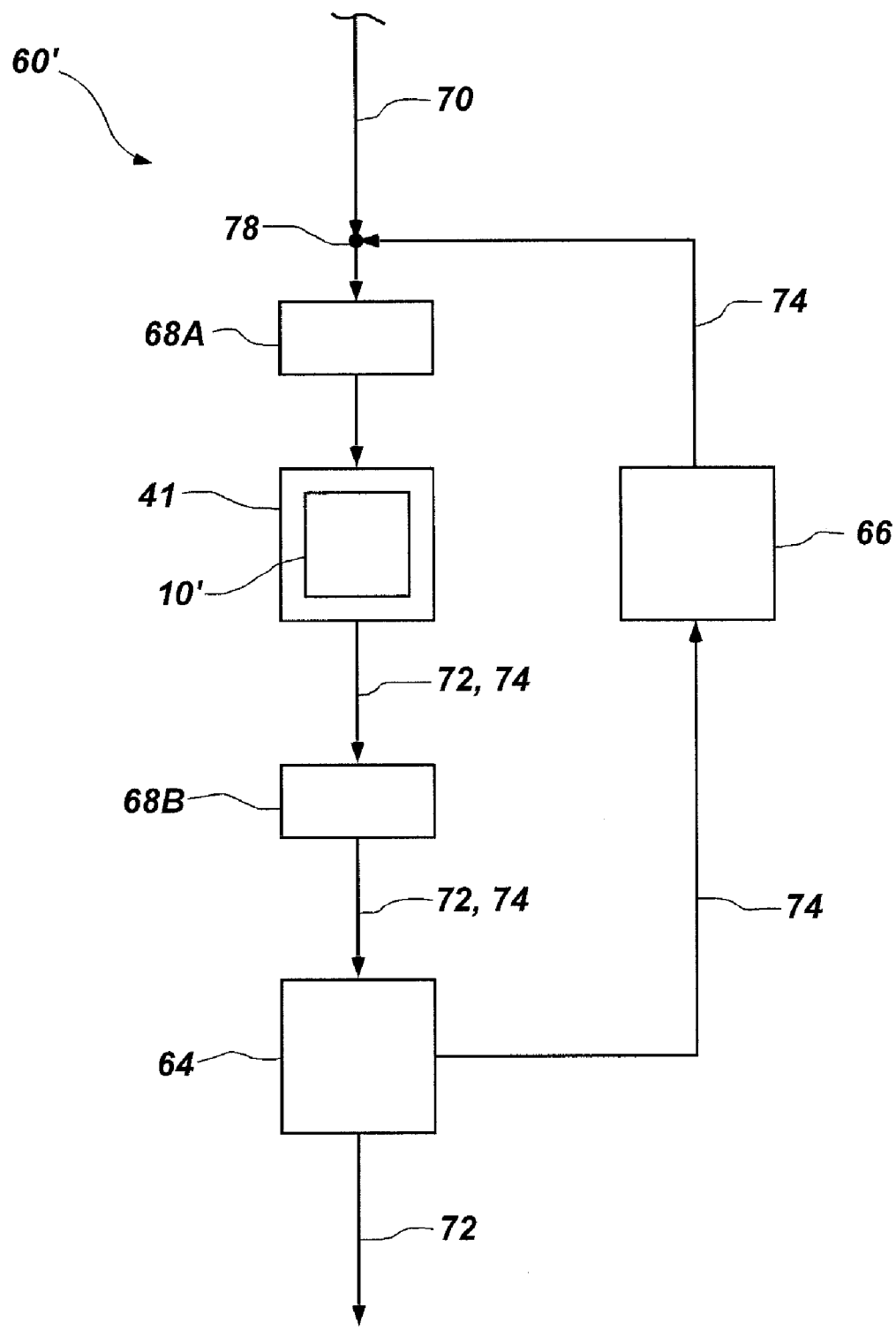
FIG. 16 is a schematic diagram of a system that embodies teachings of the present invention and includes a catalytic structure for catalyzing the formation of an alcohol from hydrogen and at least one of carbon monoxide and carbon dioxide.

The catalytic structure 10' may be used in system 60' to hydrogenate the $CO_x$ to the alcohol, as illustrated in FIG. 16. The system 60' may be substantially similar to system 60 described above, except that catalytic structure 10 is replaced by catalytic structure 10'. The container 40 may be a fixed bed reactor or a slurry bed reactor that includes the catalytic structure 10'. The system 60' may further include a heating device (not shown) configured to heat the container 40 and the catalytic structure 10' to a temperature sufficient to catalyze the hydrogenation reaction. The reaction temperature may be between about 140° C. and about 500° C., such as a temperature of about 240° C. The reactor may be pressurized to between about 0.5 megapascals (5 atmospheres) and about 10 megapascals (100 atmospheres) for the hydrogenation reaction. The reactant mixture 70 that includes hydrogen gas and the $CO_x$ (at least one of carbon monoxide (CO) and carbon dioxide ($CO_2$)) may be passed through the first heat exchanger 68A and fed to the container 40. The catalytic structure 10' may catalyze the formation of the alcohol from the hydrogen and the $CO_x$. The product mixture 72 (which may include such alcohols), together with any unreacted reactant gasses 74 and reaction byproducts, may be collected from the container 40 and passed through the second heat exchanger 68B to the gas-liquid separator 64. The gas-liquid separator 64 may be used to separate liquid hydrocarbon products of the product mixture 72 from the unreacted reactant gases 74. The unreacted reactant gases 74 may be re-pressurized as necessary using the compressor 66 and recombined with the reactant mixture 70 through the three-way valve 78, as shown in FIG. 16.

The liquid alcohol products in the product mixture 72 collected from the gas-liquid separator 64 may then be further processed as necessary or desired. For example, additional distillation equipment (not shown) may be used to purify and concentrate the various hydrocarbon components in the product mixture 72 as necessary or desired.

If methanol is produced by the hydrogenation reaction, the methanol may be used in a MTG process to produce a synfuel, as represented by Reactions [6], [7], and [8]. The methanol may be combined with a biorefinery ethanol product to produce a high octane oxygenated gasoline blendstock. The methanol may also be used in the synthesis of chemicals and synfuels, such as dimethyl ether, olefins, and gasoline. Since the conversion of the $CO_x$ to methanol is exothermic, no additional heat input is used.

In another embodiment, the catalytic structure 10' formed by the hydrothermal reaction may be dispersed within the zeolite material 12. The catalytic structure 10' may include the sheet-like structures 80 of ZnO or the spherical structures 86 of ZnO onto which particles 88 of the Cu are dispersed.

The following examples serve to explain embodiments of the present invention in more detail. These examples are not to be construed as being exhaustive or exclusive as to the scope of this invention.

EXAMPLES

Example 1

Hydrothermal Synthesis of Cu/ZnO Catalyst $Zn(NO_3)_2.6H_2O$ (4.4985 g) and $Cu(NO_3)_2.2½H_2O$ (3.8215 g) were dissolved in 50 ml of water to form Solution A. Solution B was prepared by dissolving HMTA (4.4677 g) in 25 ml of water. Solution C was prepared by dissolving sodium citrate (0.8245 g) in 50 ml of water. Solution B was added to solution A with stirring. Then, 1 ml of solution C was added to the mixture of Solution A and Solution B with stirring. The mixture was placed in a Parr acid digestion bomb, which was sealed and placed in an oven and heated to about 115° C. The hydrothermal synthesis was allowed to proceed for 1 hour (Sample 2), 2 hours (Samples 3, 5, and 7), or 3.5 hours (Samples 4, 6, and 8) (see Table 1). The Parr acid digestion bomb was removed from the oven and cooled before removing the sample. The sample was filtered, washed with water, and dried in air at a temperature of 200° C. (Samples 7 and 8) or 550° C. (Samples 2-6) (see Table 1). Samples 2-8 included a mixture of nanoscale CuO and ZnO (the precursor of the Cu/ZnO catalyst). An SEM photograph of Sample 8, illustrating the sheet-like structures 80 of ZnO and the particles 82 of CuO, is shown in FIG. 11.

The effect of the synthesis time and the drying temperature on the surface area of the precursor of the Cu/ZnO catalyst (Samples 2-8) is shown in Table 1. For comparison, CuO, ZnO, and a commercially available methanol catalyst were also tested. The commercially available methanol catalyst (Sample 1) was a KATALCO® catalyst, which is available from Johnson Matthey Catalysts, and is believed to be CuO/ZnO on an aluminum support (64 wt % CuO, 10 wt % $Al_2O_3$, 24 wt % ZnO, and 2 wt % MgO). As shown in Table 1, Sample 8 had a higher surface area than the CuO sample and the ZnO sample. Sample 8 had a lower, but comparable, surface area to Sample 1.

TABLE 1

Effect of Synthesis Time and Drying Temperature on CuO/ZnO Samples.

| Sample # | Synthesis Time (hours) | Temperature (° C.) | Surface Area ($m^2/g$) |
| --- | --- | --- | --- |
| 1 | — | — | 101.77 |
| 2 | 1 | 550 | 2.85 |
| 3 | 2 | 550[1] | 4.84 |
| 4 | 3.5 | 550 | 3.13 |
| 5 | 2 | 550[2] | 3.56 |
| 6 | 3.5 | 550 | 5.67 |
| 7 | 2 | 200 | 30.57 |
| 8 | 3.5 | 200 | 80.69 |
| CuO | 3.75 | 200 | 14.76 |
| ZnO | 3.75 | 200 | 13.44 |

Figure 17:
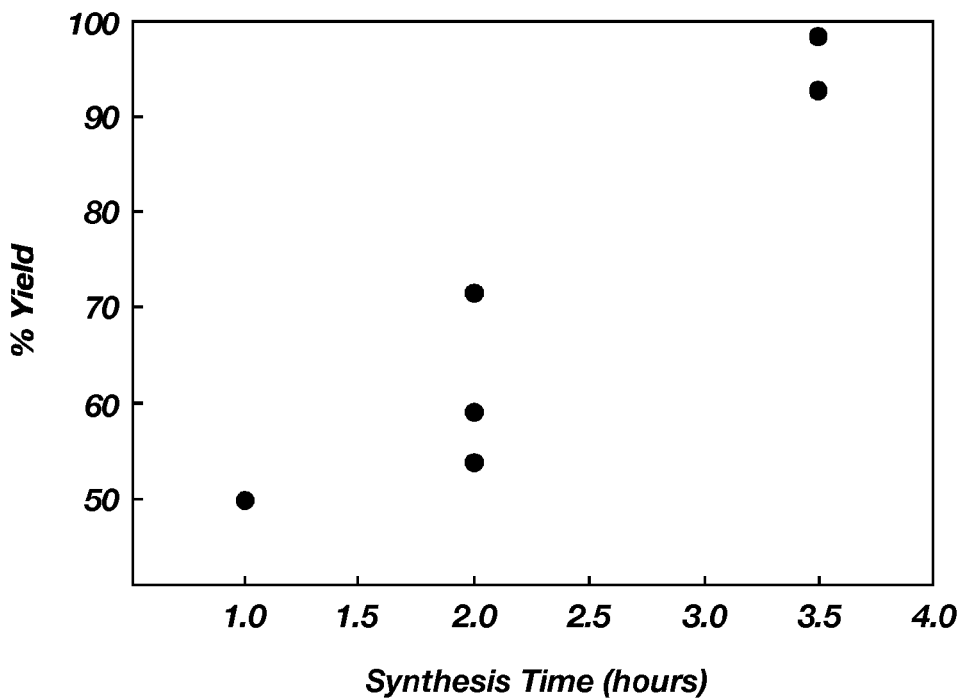
FIG. 17 is a graph illustrating catalyst yield of a catalytic structure that embodies teachings of the present invention and includes copper oxide and zinc oxide.

[1] The drying temperature was maintained at 550° C. for 5 hours
[2] The drying temperature was ramped from 100° C. to 550° C. over 9 hours and maintained at 550° C. for 5 hours The effect of synthesis time on catalyst yield (CuO/ZnO) was determined by preparing and combining Solutions A, B, and C, as described above. The mixture was placed in a Parr acid digestion bomb, which was sealed and placed in an oven maintained at 115° C. The mixture was reacted at 115° C. for 1 hour, 2 hours, or 3.5 hours. Catalyst yield (CuO/ZnO) as a function of synthesis time is shown in FIG. 17. At a synthesis time of about 3.5 hours, the catalyst yield was greater than about 90%.

Figure 18:
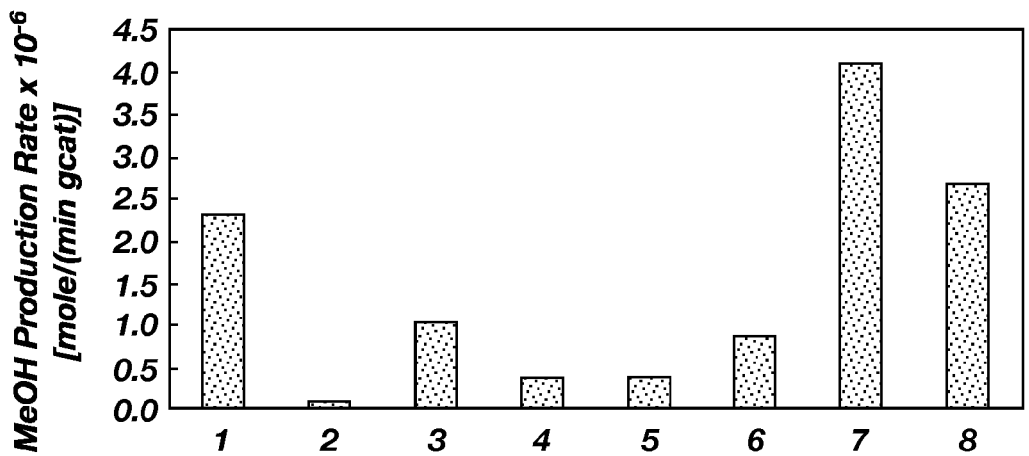
FIG. 18 is a graph illustrating the methanol production rate of a catalytic structure that embodies teachings of the present invention and includes copper and zinc oxide.

Each of Samples 1-8 was placed in a reactor and exposed to a flowing stream of 90 ml/min argon and 10 ml/min hydrogen to reduce the CuO in the precursor of the Cu/ZnO catalyst to Cu. During the reduction, the temperature was ramped from room temperature to 240° C. at 1.8° C./min and held at 240° C. overnight. Each of the Cu/ZnO catalysts and the commercially available methanol catalyst was tested to determine its ability to catalyze the reaction of $CO_2$ to methanol in the presence of hydrogen. The $CO_2$ was introduced into the reactor at a flowrate of 10 ml/min, along with 15 ml/min Ar and 30 ml/min $H_2$. The reactor included 100 mg of the catalyst to be tested and was maintained at a temperature of 240° C. The reaction was allowed to proceed for about 313 minutes. Products of the reaction were determined by gas chromatograph (GC) analysis. An SEM photograph of Sample 8, illustrating the sheet-like structures 80 of ZnO and the particles 88 of Cu, is shown in FIG. 15. The methanol production rate (moles of methanol per minute per gram of catalyst) for each catalyst is shown in FIG. 18. Samples 7 and 8 had increased methanol production compared to Sample 1 (control).

Figure 19:
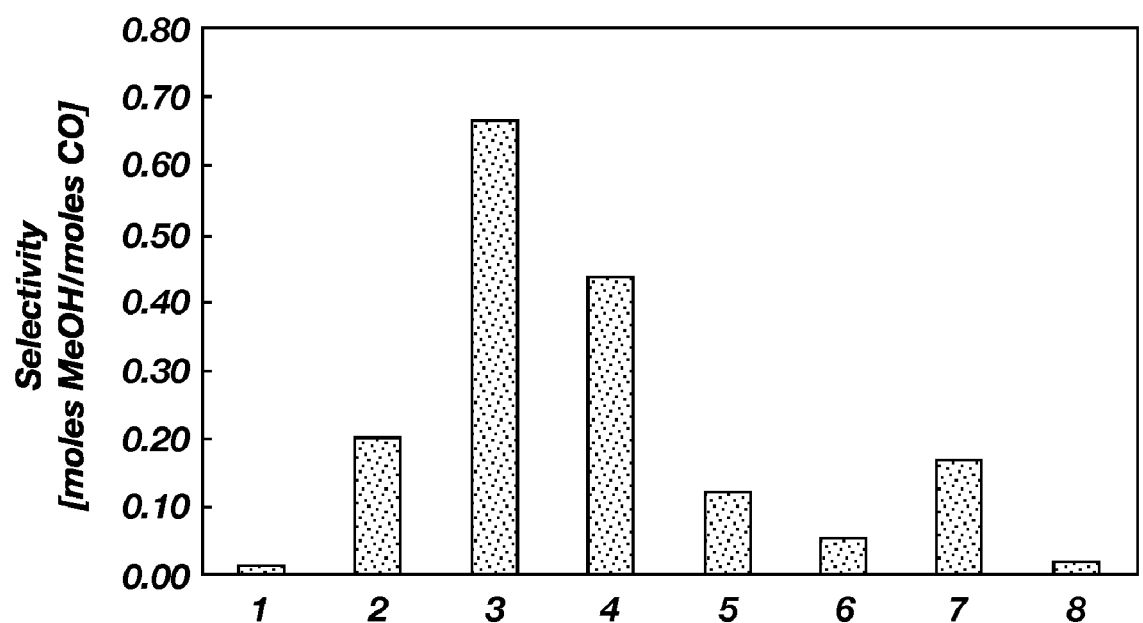
FIG. 19 is a graph illustrating methanol selectivity of a catalytic structure that embodies teachings of the present invention and includes copper and zinc oxide.

Each of catalysts 1-8, after reducing the CuO to Cu as described above, was tested to determine its selectivity for methanol relative to carbon monoxide. The $CO_2$ was introduced into the reactor at a flowrate of 10 ml/min, along with 15 ml/min Ar and 30 ml/min $H_2$. The reactor included 100 mg of the catalyst to be tested and was maintained at a temperature of 240° C. The reaction was allowed to proceed for about 313 minutes. Products of the reaction were determined by GC analysis. The selectivity in moles of methanol per moles of carbon monoxide for each catalyst is shown in FIG. 19. Sample 8 had comparable selectivity for methanol as Sample 1 (control), while the selectivities for the other samples were substantially higher.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of fabricating a catalytic structure, comprising:
heating reaction mixture comprising a zinc salt, a copper salt, a hydroxyl ion source, and a structure-directing agent in a closed vessel to produce a precursor comprising zinc oxide and copper oxide, the zinc oxide having a sheet-like morphology or a spherical morphology.

2. The method of claim 1, wherein heating a reaction mixture comprising a zinc salt, a copper salt, a hydroxyl ion source, and a structure-directing agent in a closed vessel comprises selecting the zinc salt from a compound selected from the group consisting of a zinc alkoxide, zinc acetate, zinc carbonate, zinc carbonate hydroxide, zinc citrate, zinc lactate, zinc nitrate, zinc oxalate, zinc stearate, zinc sulfate, and combinations thereof.

3. The method of claim 1, wherein heating a reaction mixture comprising a zinc salt, a copper salt, a hydroxyl ion source, and a structure-directing agent in a closed vessel comprises selecting the copper salt from a compound selected from the group consisting of copper acetate, copper acetate monohydrate, copper acetate hydrate, copper carbonate, copper formate hydrate, copper gluconate, copper hydroxide, copper methoxide, copper nitrate, copper nitrate hydrate, copper tartrate hydrate, and combinations thereof.

4. The method of claim 1, wherein heating a reaction mixture comprising a zinc salt, a copper salt, a hydroxyl ion source, and a structure-directing agent in a closed vessel comprises selecting the hydroxyl ion source from a compound selected from the group consisting of hexamethylenetetramine, ammonium hydroxide, ethylene diamine, triethanolamine, ammonia, hydrazine, and combinations thereof.

5. The method of claim 1, wherein heating a reaction mixture comprising a zinc salt, a copper salt, a hydroxyl ion source, and a structure-directing agent in a closed vessel comprises selecting the structure-directing agent from a compound selected from the group consisting of sodium citrate, potassium citrate, citric acid, poly(vinyl alcohol), poly(vinyl pyrrolidone), and combinations thereof.

6. The method of claim 1, wherein heating a reaction mixture comprising a zinc salt, a copper salt, a hydroxyl ion source, and a structure-directing agent in a closed vessel comprises heating a reaction mixture comprising zinc nitrate, copper nitrate, hexamethylenetetramine, and sodium citrate.

7. The method of claim 1, wherein heating a reaction mixture comprising a zinc salt, a copper salt, a hydroxyl ion source, and a structure-directing agent in a closed vessel comprises forming a reaction mixture comprising between about 0.01 M and about 1 M of the zinc salt, between about 0.01 M and about 1 M of the copper salt, between about 0.02 M and about 2 M of the hydroxyl ion source, and between about 0.05 mM and about 0.5 M of the surface-directing agent.

8. The method of claim 1, wherein heating a reaction mixture comprising a zinc salt, a copper salt, a hydroxyl ion source, and a structure-directing agent in a closed vessel comprises heating the reaction mixture to a temperature between about 80° C. and about 200° C.

9. The method of claim 1, wherein heating a reaction mixture comprising a zinc salt, a copper salt, a hydroxyl ion source, and a structure-directing agent in a closed vessel comprises heating the reaction mixture to a temperature between about 95° C. and about 120° C.

10. The method of claim 1, wherein heating a reaction mixture comprising a zinc salt, a copper salt, a hydroxyl ion source, and a structure-directing agent in a closed vessel comprises heating the reaction mixture for between about 1 hour and about 4 hours.

11. The method of claim 1, wherein heating a reaction mixture comprising a zinc salt, a copper salt, a hydroxyl ion source, and a structure-directing agent in a closed vessel comprises producing a mixture of zinc- and copper-containing precipitates comprising zinc oxide and copper oxide.

12. The method of claim 11, further comprising drying the mixture of zinc- and copper-containing precipitates at a temperature between about 80° C. and about 550° C.

13. The method of claim 1, further comprising reducing the copper oxide.

14. The method of claim 13, wherein reducing the copper oxide comprises forming a catalytic structure comprising copper metal and zinc oxide, wherein the zinc oxide has a sheet-like morphology or a spherical morphology.

15. The method of claim 14, wherein the catalytic structure further comprises at least one of at least one promoter and at least one additional catalytic material.

16. The method of claim 13, wherein reducing the copper oxide comprises forming a catalytic structure consisting essentially of copper metal and zinc oxide.

17. The method of claim 13, wherein reducing the copper oxide comprises forming a catalytic structure consisting of copper metal and zinc oxide.

18. A method of fabricating a catalytic structure, comprising:
heating a reaction mixture consisting of a zinc salt, a copper salt, a hydroxyl ion source, and at least one of sodium citrate, potassium citrate, citric acid, poly(vinyl alcohol), and poly(vinyl pyrrolidine) in a closed vessel to produce a precursor comprising zinc oxide and copper oxide.

19. The method of claim 18, wherein heating a reaction mixture consisting of a zinc salt, a copper salt, a hydroxyl ion source, and at least one of sodium citrate, potassium citrate, citric acid, poly(vinyl alcohol), and poly(vinyl pyrrolidine) in a closed vessel comprises selecting the zinc salt from a compound selected from the group consisting of a zinc alkoxide, zinc acetate, zinc carbonate, zinc carbonate hydroxide, zinc citrate, zinc lactate, zinc nitrate, zinc oxalate, zinc stearate, and zinc sulfate, and combinations thereof.

20. The method of claim 18, wherein heating a reaction mixture consisting of a zinc salt, a copper salt, a hydroxyl ion source, and at least one of sodium citrate, potassium citrate, citric acid, poly(vinyl alcohol), and poly(vinyl pyrrolidine) in a closed vessel comprises selecting the copper salt from a compound selected from the group consisting of copper acetate, copper acetate monohydrate, copper acetate hydrate, copper carbonate, copper formate hydrate, copper gluconate, copper hydroxide, copper methoxide, copper nitrate, copper nitrate hydrate, and copper tartrate hydrate, and combinations thereof.

21. The method of claim 18, wherein heating a reaction mixture consisting of a zinc salt, a copper salt, a hydroxyl ion source, and at least one of sodium citrate, potassium citrate, citric acid, poly(vinyl alcohol), and poly(vinyl pyrrolidine) in a closed vessel comprises selecting the hydroxyl ion source from a compound selected from the group consisting of hexamethylenetetramine, ammonium hydroxide, ethylene diamine, triethanolamine, ammonia, and hydrazine, and combinations thereof.

22. The method of claim 18, wherein heating a reaction mixture consisting of a zinc salt, a copper salt, a hydroxyl ion source, and at least one of sodium citrate, potassium citrate, citric acid, poly(vinyl alcohol), and poly(vinyl pyrrolidine) in a closed vessel comprises heating a reaction mixture consisting of zinc nitrate, copper nitrate, hexamethylenetetramine, and sodium citrate.

* * * * *

UNITED STATES PATENT AND TRADEMARK OFFICE
CERTIFICATE OF CORRECTION

PATENT NO.        : 7,592,291 B2                                              Page 1 of 2
APPLICATION NO. : 11/688930
DATED             : September 22, 2009
INVENTOR(S)       : Harry W. Rollins, Lucia M. Petkovic and Daniel M. Ginosar It is certified that error appears in the above-identified patent and that said Letters Patent is hereby corrected as shown below:

On the title page:
In ITEM (73) Assignee:                    change "Batelle" to --Battelle--

In ITEM (56) References Cited
OTHER PUBLICATIONS
page 2, 1st COLUMN, 3rd entry             change "<<hhttp://en." to --<<http://en.--
page 2, 1st COLUMN, 8th entry             change "Fujiwara, et al.," to --Fujiwara et al.,--

COLUMN 1 LINES 19-22                      delete entire paragraph and replace with --This invention was made with government support under Contract No. DE-AC07-05ID14517 awarded by the United States Department of Energy. The government has certain rights in this invention.--

COLUMN 2   LINE 65                        change "5th ed.," to --5th Rev. ed.,--
COLUMN 4   LINE 24                        change "FIGS. 4-7" to --FIGS. 4 through 7--
COLUMN 4   LINE 27                        change "reactor" to --container--
COLUMN 4   LINE 30                        change "reactor" to --container--
COLUMN 5   LINES 11-12                    change "T atoms" to --T-atoms--
COLUMN 5   LINE 25                        change "include a" to --includes a-- and change "have a" to --has a--
COLUMN 6   LINE 24                        change "representations which" to --representations, which--
COLUMN 6   LINE 61                        change "5th ed.," to --5th Rev. ed.,--
COLUMN 8   LINE 34                        change "FIGS. 1-3," to --FIGS. 1 through 3,-- and change "FIGS. 4-7." to --FIGS. 4 through 7.--
COLUMN 9   LINE 53                        change "may converted" to --may be converted--
COLUMN 10  LINE 29-30                     change "micropores 18 and/or" to --micropores 18 (FIG. 2) and/or--
COLUMN 10  LINE 37                        change "FIGS. 1-3." to --FIGS. 1 through 3.--
COLUMN 10  LINE 60                        change "FIGS. 1-3." to --FIGS. 1 through 3.--
COLUMN 11  LINE 12                        change "FIGS. 1-3." to --FIGS. 1 through 3.--
COLUMN 11  LINE 13                        change "container 40," to --reactor 41,--

Signed and Sealed this

Thirtieth Day of November, 2010

David J. Kappos
*Director of the United States Patent and Trademark Office*

CERTIFICATE OF CORRECTION (continued)
U.S. Pat. No. 7,592,291 B2

| | |
|---|---|
| COLUMN 11  LINE 15 | change "container 40" to --reactor 41-- |
| COLUMN 11  LINE 19 | change "container 40," to --reactor 41,-- |
| COLUMN 11  LINE 21 | change "container 40." to --reactor 41.-- |
| COLUMN 11  LINE 23 | change "container 40" to --reactor 41-- |
| COLUMN 11  LINE 25 | change "container 40" to --reactor 41-- |
| COLUMN 11  LINE 27 | change "container 40" to --reactor 41-- |
| COLUMN 11  LINE 33 | change "container 40." to --reactor 41.-- |
| COLUMN 11  LINE 36 | change "by product" to --byproduct-- |
| COLUMN 11  LINE 37 | change "manufacture," to --manufacturing,-- |
| COLUMN 11  LINE 51 | change "container 40" to --reactor 41-- |
| COLUMN 11  LINE 56 | change "gasses 74" to --gases 74-- |
| COLUMN 11  LINE 65 | change "mixture 72 as necessary" to --mixture 72, as necessary-- |
| COLUMN 14  LINE 36 | change "("wt  %") and about 90 wt %" to --("wt%") and about 90 wt%-- |
| COLUMN 14  LINE 37 | change "10wt% and about 90wt%" to --10 wt% and about 90 wt%-- |
| COLUMN 15  LINE 66 | change "container 40" to --reactor 41-- |
| COLUMN 16  LINE 2 | change "container 40" to --reactor 41-- |
| COLUMN 16  LINE 6 | change "The reactor may" to --The reactor 41 may-- |
| COLUMN 16  LINE 7 | change "0.5 megapascals" to --0.5 megapascal-- |
| COLUMN 16  LINE 12 | change "container 40." to --reactor 41.-- |
| COLUMN 16  LINE 16 | change "gasses 74" to --gases 74-- |
| COLUMN 16  LINE 17 | change "container 40" to --reactor 41-- |
| COLUMN 16  LINE 61 | change "solutionA" to --solution A-- |
| CLAIM 1, COLUMN 18, LINE 29 | change "heating reaction" to --heating a reaction-- |